United States Patent
Brophy et al.

(10) Patent No.: US 8,106,249 B2
(45) Date of Patent: Jan. 31, 2012

(54) CATALYTIC OXIDATIVE DEHYDROGENATION, AND MICROCHANNEL REACTORS FOR CATALYTIC OXIDATIVE DEHYDROGENATION

(75) Inventors: John H. Brophy, Avon (GB); Kai Jarosch, Bexley, OH (US); Terry J. Mazanec, Solon, OH (US); Matthew B. Schmidt, Columbus, OH (US); Laura J. Silva, Dublin, OH (US); Anna Lee Tonkovich, Marysville, OH (US); Fred Pesa, Aurora, OH (US); David J. Hesse, Columbus, OH (US)

(73) Assignee: Velocys, Plain City, OH (US)

( * ) Notice: Subject to any disclaimer, the term of this patent is extended or adjusted under 35 U.S.C. 154(b) by 11 days.

(21) Appl. No.: 12/825,321

(22) Filed: Jun. 28, 2010

(65) Prior Publication Data

US 2011/0152597 A1    Jun. 23, 2011

Related U.S. Application Data

(62) Division of application No. 12/135,167, filed on Jun. 7, 2008, now Pat. No. 7,744,829, which is a division of application No. 10/441,921, filed on May 19, 2003, now Pat. No. 7,402,719.

(60) Provisional application No. 60/388,635, filed on Jun. 13, 2002.

(51) Int. Cl.
*C07C 5/32* (2006.01)
*B01J 8/00* (2006.01)

(52) U.S. Cl. ........ 585/658; 585/616; 585/654; 422/603; 422/606

(58) Field of Classification Search ................ 585/500, 585/616, 658, 654; 422/603, 606
See application file for complete search history.

(56) References Cited

U.S. PATENT DOCUMENTS

| | | | |
|---|---|---|---|
| 4,524,236 A | 6/1985 | McCain | |
| 4,739,124 A | 4/1988 | Ward | |
| 4,760,210 A | 7/1988 | Sweeney | |
| 4,940,826 A | 7/1990 | Font Freide et al. | |
| 5,254,788 A | 10/1993 | Gartside et al. | |
| 5,593,935 A | 1/1997 | Golunski et al. | |
| 5,599,510 A * | 2/1997 | Kaminsky et al. | 585/500 |
| 5,811,062 A | 9/1998 | Wegeng et al. | |
| 5,935,489 A | 8/1999 | Hershkowitz et al. | |
| 5,997,826 A | 12/1999 | Lodeng et al. | |
| 6,117,578 A | 9/2000 | Lesieur | |
| 6,166,283 A | 12/2000 | Bharadwaj | |
| 6,190,624 B1 | 2/2001 | Romantier | |
| 6,274,113 B1 | 8/2001 | Heyse et al. | |
| 6,315,977 B1 | 11/2001 | Cantacuzene | |
| 6,365,543 B1 | 4/2002 | Schmidt et al. | |
| 6,488,838 B1 | 12/2002 | Tonkovich et al. | |
| 6,515,146 B1 | 2/2003 | Perregaard et al. | |
| 6,566,573 B1 | 5/2003 | Bharadwaj | |
| 6,709,640 B1 | 3/2004 | Romantier et al. | |

(Continued)

FOREIGN PATENT DOCUMENTS
WO     WO 01/54807     8/2001

*Primary Examiner* — Nina Bhat
(74) *Attorney, Agent, or Firm* — Frank Rosenberg

(57) ABSTRACT

Methods of oxidative dehydrogenation (ODH) is provided wherein conducting ODH in microchannels has unexpectedly been found to yield superior performance when compared to the same reactions at the same conditions in larger reactors. ODH methods employing a Mo—V—Mg—O catalyst is also described. Microchannel apparatus for conducting ODH is also disclosed.

16 Claims, 7 Drawing Sheets

U.S. PATENT DOCUMENTS

| | | |
|---|---|---|
| 6,756,340 B2 | 6/2004 | Voskoboynikov et al. |
| 6,756,515 B2 | 6/2004 | Rende et al. |
| 7,999,144 B2 * | 8/2011 | Tonkovich et al. ............ 585/658 |
| 8,003,073 B2 * | 8/2011 | Pez et al. ...................... 423/651 |
| 2003/0007904 A1 | 1/2003 | Tonkovich et al. |
| 2004/0034266 A1 | 2/2004 | Brophy et al. |
| 2004/0220434 A1 | 11/2004 | Brophy et al. |

* cited by examiner

CATALYTIC OXIDATIVE DEHYDROGENATION, AND MICROCHANNEL REACTORS FOR CATALYTIC OXIDATIVE DEHYDROGENATION

RELATED APPLICATIONS

This application is a divisional of Ser. No. 12/135,167 filed Jun. 7, 2008, now U.S. Pat. No. 7,744,829, incorporated herein by reference as if reproduced in full below, which was a divisional of Ser. No. 10/441,921 filed May 19, 2003, now U.S. Pat. No. 7,402,719. In accordance with 35 U.S.C. sect. 119(e), this application claims priority to U.S. Provisional Application Nos. 60/388,635, filed Jun. 13, 2002, which is incorporated herein as if reproduced in full below.

FIELD OF THE INVENTION

The present invention relates to the production of olefinic hydrocarbons by oxidative dehydrogenation. More particularly, this invention relates to catalytic oxidative dehydrogenation of hydrocarbons to yield olefins, and preferably, to the production of light olefins from light hydrocarbons and to the production of styrene from ethylbenzene.

BACKGROUND OF THE INVENTION

Olefinic hydrocarbons, such as ethylene, propene, butene, and isobutene, are critical intermediates in the petrochemical industry. In order to satisfy market demand, substantial efforts have been invested in the production of such compounds by conventional thermal steam cracking of alkanes and naphtha and by catalytic dehydrogenation methods. However, conventional steam cracking is equilibrium limited and requires very high temperatures (over 700° C.) to achieve a high enough conversion of ethane to be economically viable. Even so, temperatures are limited by available alloys to temperatures at which single pass yields are still relatively low. Steam cracking also requires the input of large amounts of heat to drive the endothermic gas phase cracking reaction. Because of the equilibrium limitations, steam cracking must be carried out at low pressures typically 1 atmosphere or less and requires cooling and compression of the product stream to effect separation and recovery of the olefins produced.

Conventional catalytic dehydrogenation has similar disadvantages, including the need for high reaction temperatures (e.g., 550 to over 700° C. depending on the feedstock), the deactivation of the catalyst by coke formation, and the consequent need for continuous or periodic catalyst regeneration at frequent intervals throughout the process. In addition, there are thermodynamic limitations in conventional dehydrogenation. These thermodynamic limitations are due to the fact that conversion in conventional dehydrogenation processes are equilibrium limited, and require high temperature and low pressure to achieve high single pass yields. As a result of these substantial drawbacks, the petroleum industry has sought a solution to the demand for olefinic hydrocarbons in the use of autothermal cracking and oxidative dehydrogenation methods.

In autothermal cracking, oxygen or air is added to the feed and partially combusts part of the feed in situ generating the high temperatures required to thermally crack the remaining feedstock. In some variants a catalyst is used to support combustion with the catalyst being in the form of a fixed bed or a fluidized or spouted bed. Fixed beds are preferred to reduce catalyst attrition. In some cases hydrogen is co-fed with the feedstock and is found to increase olefin yields. Autothermal cracking usually takes place at high temperatures (550-1200° C.) and requires very short reaction times and rapid quenching of the products to preserve the olefinic products and prevent further undesirable reactions. Even so, by products are formed including carbon oxides. At higher pressure, yields of undesirable by-products increase. At very high temperatures as encountered in some autothermal processes, hydrocarbon cracking to methane also reduces selectivity to useful olefinic products.

Catalytic oxidative dehydrogenation is, in principle, not subject to many of the problems associated with conventional steam cracking or catalytic dehydrogenation because of the presence of oxygen in the reaction mixture. Oxidative dehydrogenation (ODH) uses oxygen to react with the hydrogen released from the hydrocarbon, in situ, so that the aforementioned equilibrium limitation is removed, and high single pass yields can be achieved. The reaction is exothermic overall and does not require a supply of heat as in endothermic dehydrogenation reactions. Generally, in a catalytic oxidative dehydrogenation process, the reactants (hydrocarbon and an oxygen-containing gas) are passed over the fixed bed catalyst directly to produce olefin product. Typically, the hydrocarbon is a saturated hydrocarbon such as ethane or a mixture of saturated hydrocarbons. The hydrocarbon may be gaseous or liquid at ambient temperature and pressure but is typically gaseous.

An example of an alkene which can be formed via an oxidative dehydrogenation process, is ethylene. The latter process is attractive for many reasons. For example, compared to thermal cracking, high ethane conversion can be achieved at moderate temperatures (300-1000° C.) by catalytic oxidative dehydrogenation. Unlike thermal cracking and catalytic dehydrogenation, catalytic ODH is exothermic, requiring no additional heat, beyond feed pre-heat, to sustain reaction. Furthermore, in contrast to catalytic dehydrogenation, catalyst deactivation by coke formation should be minimal in ODH because of the presence of oxygen in the reactor feed. Other alkanes can similarly be oxidatively dehydrogenated.

Although there are no reported commercial ODH processes operating at the present time, there is a high level of commercial interest. Activity has focused on ethane, propane and isobutane ODH, and patents to same have issued. Representative of these patents are the following US patents, all of which are herein incorporated by reference: U.S. Pat. No. 4,524,236; U.S. Pat. No. 5,162,578; U.S. Pat. No. 5,593,935; U.S. Pat. No. 5,997,826; U.S. Pat. No. 6,313,063; U.S. Pat. No. 6,281,378; U.S. Pat. No. 6,239,325; U.S. Pat. No. 6,235,678; U.S. Pat. No. 6,130,183; U.S. Pat. No. 6,355,854 and U.S. Pat. No. 6,310,241.

Industrial interest has stimulated investigations into new catalysts and methods for improved performance (e.g., conversion and selectivity) for the oxidative dehydrogenation of alkanes. U.S. Pat. No. 4,524,236 reports high conversion (73%) and high selectivity (71%) for ethane ODH but these results were obtained only by diluting the ethane/oxygen feed with helium as 85.5% of the feedstock. Others have achieved high yields by co-feeding hydrogen with the hydrocarbon feedstock and oxygen (see U.S. Pat. No. 5,997,826).

In U.S. Pat. No. 4,524,236 McCain describes a process for the low temperature catalytic oxydehydrogenation of ethane to ethylene in a gas phase and featuring the use of a catalyst containing Mo/V/Nb/Sb and an additional element.

There have been different approaches to adding oxygen to the ODH reaction. Lodeng et al. in U.S. Pat. No. 5,997,826 describes a process for converting C3 and C4 paraffins to olefins by a sequential reactor that contains at least three zones, a catalytic dehydrogenation process zone, an oxygen admixing zone, and a catalytic oxidation zone, wherein the flow velocity in the admixing zone is higher than in the catalyst zones. Ward in U.S. Pat. No. 4,739,124 discloses mixing oxygen between stages.

In a process for catalytic selective oxidation of a hydrocarbon, Perregaard et al. in U.S. Pat. No. 6,515,146 discloses a reactor in which oxygen flows into a 7 mm inner diameter tube through the porous alumina tube walls and into the catalyst bed held within the tubes. No mention is made of the useful of this approach in ODH.

Beretta et al. in "Production of olefins via oxidative dehydrogenation of light paraffins at short contact times," Catalysis Today, 64 pp 103-111 (2001) reported testing of a $Pt/Al_2O_3/Fe$—Cr catalyst in an annular reactor. Comparative tests without catalyst showed no proof that the Pt catalyst contributed to the selective oxidation of ethane to ethene; however, there was strong proof "that the catalyst was active in non-selective oxidation reactions, and that gas-phase oxidative pyrolysis was a fast process with very high ethene selectivities." The authors concluded that the Pt-containing catalyst seemed to be mainly active in the total oxidation of ethane to $CO_x$.

Several workers have described oxidative dehydrogenation in catalyst monoliths positioned in conventional reactors. See, U.S. Pat. Nos. 4,940,826, 6,166,283, and 6,365,543. They do not suggest the use of monoliths in microchannel reactors or any microchannel advantages.

As compared to conventional, fixed bed reactors, microchannel reactors have been found to suppress thermal gradients; however, at comparable catalyst bed temperatures, the microchannel reactor did not improve performance. Steinfeldt et al. in "Comparative Studies of the Oxidative Dehydrogenation of Propane in Micro-Channels Reactor Module and Fixed-Bed Reactor," Studies in Surface Science and Catalysis, pp 185-190 (2001) conducted testing of ODH in a microchannel reactor over a $VOx/Al_2O_3$ catalyst. To minimize temperature gradients, the catalyst was diluted with quartz in a ratio of 1:9. The authors reported that "the use of micro-channels reactor module allowed isothermal operation at all reaction conditions." The authors concluded that the "micro-channel reactor module and fixed bed reactor show approximately the same catalytic results under isothermal conditions."

Despite extensive research, there remains a need for new oxidative dehydrogenation catalysts, catalytic systems, and methods that achieve high conversion at high selectivity, such that the yield of the desired olefin is maximized, and extraneous oxidative side reactions are minimized. Such extraneous oxidative side reactions may include the conversion of starting hydrocarbon, e.g., alkane, into carbon oxides (CO and/or $CO_2$), and/or conversion of desired product alkene into carbon oxides.

SUMMARY OF THE INVENTION

According to the scientific literature, the performance of the oxidative dehydrogenation reaction in microchannels did not differ from the reaction in conventional fixed bed reactors operating at the same temperature. Thus, in view of the fact that microchannel apparatus is generally more expensive than conventional equipment, there appeared to be no reason to conduct oxidative dehydrogenation in microchannel apparatus. Despite this discouraging background, we proceeded to test oxidative dehydrogenation reactions in microchannel reactors. Surprisingly, we found that conducting the oxidative dehydrogenation reaction in microchannel apparatus produced significantly superior results as compared to the same reaction in larger, more conventionally-sized apparatus.

In one aspect, the invention provides a method for catalytic oxidative dehydrogenation of a gaseous hydrocarbon, comprising: flowing a hydrocarbon-containing fluid and a source of oxygen into a microchannel; wherein a catalyst is present in the microchannel; reacting the hydrocarbon-containing fluid and the source of oxygen, in the microchannel, in a temperature range of 335 to 1000° C., to form water and at least one alkene and/or aralkene; and removing heat into an adjacent heat exchanger. In preferred embodiments, heat is removed into an adjacent heat exchanger by (a) cooling the microchannel by flowing a coolant fluid (which could be a reactant stream) through an adjacent cooling chamber to convectively cool the reaction microchannel, or (b) conducting a simultaneous endothermic reaction in adjacent channel(s) to remove heat, or (c) performing a phase change in adjacent channel(s), preferably microchannel(s), to provide additional heat removal beyond that provided by convective heat exchange in adjacent channel(s).

In another aspect, the invention provides a method for catalytic oxidative dehydrogenation of a gaseous hydrocarbon, comprising: flowing a hydrocarbon-containing fluid and a source of oxygen into a microchannel; wherein a catalyst is present in the microchannel; reacting the hydrocarbon-containing fluid and the source of oxygen, in the microchannel, in a temperature range of 335 to 1000° C., to form water and at least one alkene and/or aralkene; and quenching the stream formed after reacting the hydrocarbon-containing fluid and the source of oxygen.

In a further aspect, the invention provides a method for catalytic oxidative dehydrogenation of a gaseous hydrocarbon, comprising: flowing a hydrocarbon-containing fluid and a source of oxygen into a microchannel; wherein a catalyst is present in the microchannel; reacting the hydrocarbon-containing fluid and the source of oxygen, in the microchannel, in a temperature range of 335 to 1000° C., to form water and at least one alkene and/or aralkene; and feeding oxygen into the microchannel at multiple points along the channel length.

In another aspect, the invention provides a method for catalytic oxidative dehydrogenation of a gaseous hydrocarbon, comprising: flowing a hydrocarbon-containing fluid and a source of oxygen into a microchannel; wherein a catalyst is present in the microchannel; reacting the hydrocarbon-containing fluid and the source of oxygen, in the microchannel, in a temperature range of 335 to 1000° C., to form water and at least one alkene and/or aralkene; and wherein said method is characterized by superior conversion, selectivity and/or yield, such that, as compared to a reaction conducted under the same conditions (reactant feed composition, oxidant, diluent, ratios of feed/oxidant/diluent (with diluent level as close as practicable), contact time, pressure, catalyst bed temperature, catalyst composition and form) in a 1.0 cm inner diameter quartz tube with no active cooling and pre-mixed hydrocarbon and oxidant (that is, no staged oxidant), the results of the method exhibits one or more of the following: (a) an at least 20% relative higher ratio of selectivities of $CO/CO_2$; or (b) an at least 10% relative higher conversion of hydrocarbon; or (c) an at least 10% relative higher yield of olefins; or (d) an at least 10% relative higher selectivity to olefins; or (e) an at least 10% relative lower selectivity of carbon dioxide. By "relative" is meant in comparison to the quartz tube, for example, if the method in a quartz tube produced a 10% conversion, an 11% conversion would be 10% higher relative conversion. This method differs from ODH through a monolith in a conventional reactor that would not necessarily produce enhanced results. In contrast, persons ordinarily skilled in this technology would, in light of the teachings set forth herein, be able through no more than routine experimentation to identify suitable operating conditions to obtain the claimed enhanced results.

In another aspect, the invention provides a method of oxidatively dehydrogenating a gaseous hydrocarbon, comprising: flowing a hydrocarbon-containing fluid and a source of oxygen into a microchannel; wherein an oxidative dehydrogenation catalyst is present in the microchannel; reacting the hydrocarbon-containing fluid and the source of oxygen, in the microchannel, in a temperature range of 300 to 1000° C., to form water and at least one alkene and/or aralkene; wherein the hydrocarbon comprises an alkane or aralkane, and wherein diluent, if present, constitutes 0.25 or less, as a volume fraction, of total fluid flow through the microchannel.

In a further aspect, the invention provides a method of oxidatively dehydrogenating a gaseous hydrocarbon, comprising: flowing a hydrocarbon-containing fluid and a source of oxygen into a microchannel; wherein an oxidative dehydrogenation catalyst is present in the microchannel; reacting the hydrocarbon-containing fluid and the source of oxygen, in the microchannel, in a temperature range of 300 to 1000° C., to form water and at least one alkene and/or aralkene; wherein the hydrocarbon comprises an alkane or aralkane, and wherein at least 10% of the hydrocarbon is converted to an alkene and/or aralkene; and wherein total hydrocarbon feed flow through the microchannel is at a LHSV of about 32 or greater.

In a further aspect, the invention provides a method of oxidatively dehydrogenating a gaseous hydrocarbon, comprising: flowing a hydrocarbon-containing fluid and a source of oxygen into a microchannel; wherein an oxidative dehydrogenation catalyst is present in the microchannel; reacting the hydrocarbon-containing fluid and the source of oxygen, in the microchannel, in a temperature range of 300 to 1000° C., to form water and at least one alkene and/or aralkene; wherein the hydrocarbon comprises an alkane or aralkane, and wherein at least 10% of the hydrocarbon is converted to an alkene and/or aralkene; and wherein diluent, if present, constitutes 0.25 or less, as a volume fraction, of total fluid flow through the microchannel, and wherein total hydrocarbon feed flow through the microchannel is at a LHSV of about 1 or greater.

The invention also provides a method of oxidatively dehydrogenating a gaseous hydrocarbon with reduced gas phase reactions, comprising: flowing a hydrocarbon-containing fluid and a source of oxygen into a microchannel; wherein an oxidative dehydrogenation catalyst is present in the microchannel; and wherein the hydrocarbon-containing fluid and the source of oxygen are combined immediately before contacting the catalyst such that precatalyst contact time is 150 ms or less.

In yet another aspect, the invention provides a method of oxidatively dehydrogenating a gaseous hydrocarbon with reduced gas phase reactions, comprising: flowing a hydrocarbon-containing fluid and a source of oxygen into a microchannel; wherein an oxidative dehydrogenation catalyst is present in the microchannel; and wherein the combined pressure of hydrocarbon-containing fluid and the source of oxygen in a feed stream is at least 10 atmospheres (when measured under standard conditions) and the precatalyst contact time of the hydrocarbon-containing fluid or the source of oxygen at a temperature of 300° C. or more is 15 ms or less.

In another aspect, the invention provides a method of oxidatively dehydrogenating a gaseous hydrocarbon, comprising: flowing a hydrocarbon-containing fluid and a source of oxygen into a reaction chamber; wherein an oxidative dehydrogenation catalyst is present in the reaction chamber; wherein the oxidative dehydrogenation catalyst comprises an oxide catalyst comprising Mg, V and Mo, wherein the molar ratio of Mo:V is in the range of 0.5 to 2; reacting the hydrocarbon-containing fluid and the source of oxygen, in the reaction chamber, to form water and at least one alkene and/or aralkene.

In another aspect, the invention provides apparatus for oxidatively dehydrogenating a hydrocarbon, comprising: a microchannel reaction chamber; and an oxidative dehydrogenation catalyst disposed in the microchannel reaction chamber; and comprising: an oxygen channel adjacent to said microchannel reaction chamber and separated by an oxygen channel wall, wherein apertures through said oxygen channel wall form passageways between the oxygen channel and the reaction chamber.

In another aspect, the invention provides apparatus for oxidatively dehydrogenating a hydrocarbon, comprising: a microchannel reaction chamber; and an oxidative dehydrogenation catalyst disposed in the microchannel reaction chamber comprises one of the following forms:
  a) a particulate catalyst; or
  b) a porous insert; or
  c) a catalyst wall coating comprising a first layer formed between a reaction chamber wall and a second layer; wherein the reaction chamber wall, first layer and second layer have different compositions, wherein the first layer has a thickness of at least 0.1 micrometers, more preferably at least 1.0 micrometers.

In a further aspect, the invention provides a catalytic system for oxidatively dehydrogenating a hydrocarbon, comprising: a reaction chamber; and an oxidative dehydrogenation catalyst disposed in the reaction chamber; wherein the system is characterizable by a catalytic activity such that when propane and $O_2$, with no diluents, in a 1:1 ratio are fed into the reaction chamber at an LHSV of 32 and a catalyst temperature of 580° C., there is a propane conversion of at least 30% and an olefin yield of at least 20%.

As exemplified in the aspect above, any of the systems and methods can, in some cases, be characterized in conjunction with properties such as conversion, yield and/or selectivity. These properties can be selected from any of the values in the descriptions of preferred embodiments or from the data in the Examples section.

Advantages provided by various embodiments of the present invention may include one or more of the following: relatively high levels of alkane(s) and/or aralkane(s) conversion and high selectivity to alkene(s) and/or aralkene(s); relatively low selectivity to by-products, such as carbon monoxide or carbon dioxide; and the ability to conduct oxidative dehydrogenation without diluents added to either the feed and/or the catalyst—thus providing a more efficient and compact technique.

Other advantages of the process of the present invention include: maximization of intercontact of the source of oxygen, the hydrocarbon, and the catalyst material; and, minimization of homogenous gas-phase unselective reactions, such as those which convert starting and/or product hydrocarbon to carbon oxides ($CO_x$).

Further advantages which may accrue to the processes of the present invention include the possibility of process intensification. Conventional ODH and autothermal cracking processes of the prior art are often operated under condition of reactant dilution to prevent runaway reactions (and prevent explosions), while the process of the present invention can be operated, if desired, under more intensive conditions leading to greater throughput. By combining catalytic microchannel and adjacent heat exchangers it is possible to operate at feed/oxygen ratios that would conventionally lead to high temperatures and loss of selectivity, but by removing heat rapidly through heat exchange with the heat removal channels, the temperature in the catalytic channels can be kept relatively low (in some embodiments below 700° C., or below 600° C., or below 500° C.), thus maximizing selectivity to desired olefin products. The inventive process can be operated very nearly in a thermally neutral mode, wherein the heat released by the oxidation chemistry very nearly matches the heat consumed in the cracking reactions, thus minimizing the need to remove or add large amounts of heat to the reactor.

GLOSSARY

"Adjacent" means directly adjacent such that a wall separates two channels or chambers; this wall may vary in thickness; however, "adjacent" chambers are not separated by an intervening chamber that would interfere with heat transfer between the chambers.

By "including" is meant "comprising", however, it will be understood that the terms "consists of" or "consists essentially of", may alternatively be used in place of "comprising" or "including" to describe more limited aspects of the invention.

"Integrated" means all the components are within the same structure wherein the exhaust zones are directly connected to the reaction chambers.

Liquid hourly space velocity (LHSV) is defined based on the liquid volumetric flow and the reaction chamber volume. Reaction chamber volume is defined as the volume of a process channel where catalyst is present and the temperature is sufficiently high for dehydrogenation to occur. Reaction chamber volume is the wall-to-wall volume and includes catalyst volume (including pore volume, and, if present, interstitial volume), and, if present, the volume of a bulk flow path or paths through or by the catalyst. For dehydrogenation of isobutene, a "sufficiently high" temperature will typically be at least about 400° C., for dehydrogenation of propane, typically at least about 450° C. To calculate LHSV, GHSV (h-1), defined as volumetric flow rate of gas of hydrocarbon (ml/h) per volume catalyst (ml), is calculated and then it is divided by a factor that relates the volume of a quantity of the feed in the gas phase to the volume of the same quantity of the feed as a liquid (230 for propane). This factor takes into account the difference in the density of the hydrocarbon in liquid and gas phase.

Contact time is calculated as 3600/GHSV (hydrocarbon) and has dimensions of seconds. Contact time is defined by the volume of the reaction chamber divided by the volumetric feed flow rate of the reactant composition. The volumetric feed flow rate is the sum of the hydrocarbon inlet flow rate(s) and the inlet oxidant flow rate(s) taken as if they were gasses at a temperature of 0° C. and a pressure of 1 atmosphere.

"A reactant stream containing a hydrocarbon" can also be termed "a hydrocarbon stream," and, in the context of the present invention, these terms mean the entire gas stream (not merely a selected portion thereof) entering a reaction chamber(s).

"ODH" is oxidative dehydrogenation.

"Autothermal cracking" is oxidative dehydrogenation which requires minimal or no net heat input to or removal from the system.

"Thermally neutral" means a process in which the difference between the enthalpy of the product mixture leaving the reactor zone and the enthalpies of the reactants entering the reactor zone (including oxidant and diluent) is less than 25% (in some embodiments 10% or less and in some embodiments 5% or less) of the combined reactant enthalpies. In some embodiments, the methods described herein are thermally neutral.

Definitions of the performance parameters used herein, are as follows. "Percent conversion" refers to the moles of carbon in the organic compound(s) to be dehydrogenated (e.g., moles of carbon in the alkane) that are consumed, based on the moles of carbon in the said organic compound(s) fed to the reactor. "Percent selectivity" refers to the moles of carbon in the products (e.g., alkene) formed based on the moles of carbon consumed. "Percent yield" refers to the moles of carbon in the desired product(s) (e.g., alkene) formed based on the moles of carbon fed. For reaction mixtures of ethane, propane or butane, desired products are ethene, propene, and butenes, respectively. Percent selectivity and percent yield are based on carbon. To give a hypothetical example, a reaction mixture containing 2 moles of hexane and 1 mole ethane that results in a product mixture containing 1 mole hexane, 1 mole ethene, 0.5 mole hexene, 2 mole $CO_2$ and 0.33 mole propene would have a 57% carbon conversion with a (6 mol C)/(8 mol C)=75% selectivity to olefins (37.5% hexene, 12.5% propene, 25% ethene) and 42.8% yield of olefins (21.4% hexene yield, 7.1% propene, 14.3% ethene).

DESCRIPTION OF THE INVENTION

Figure 1A:
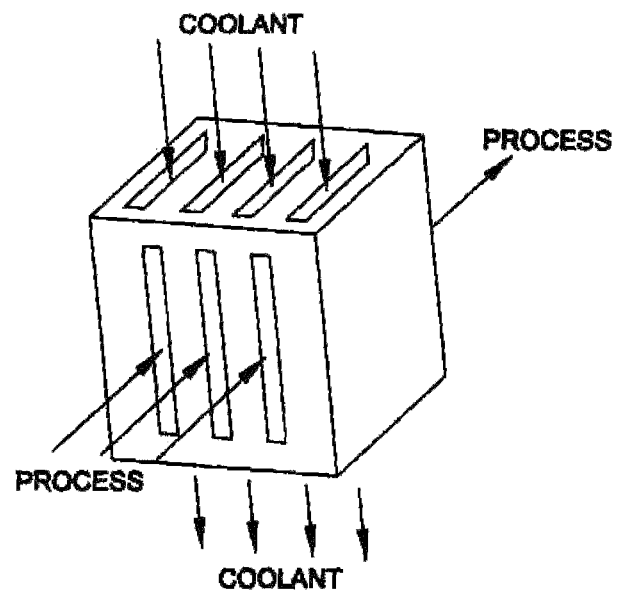
FIG. 1A illustrates a cross-flow microchannel reactor for ODH. ODH catalysts can be placed in the process channels as either a coating, an insertable felt or foam, or packed powders. A coolant could alternatively be oriented as co-flow or counter-flow. The coolant could be a gas stream, a liquid stream such as hot oil or molten salt, a phase change liquid, or an endothermic reaction such as reforming.

The invention includes a method for catalytic oxidative dehydrogenation of a hydrocarbon. In this method, a hydrocarbon-containing mixture (the mixture is or contains a fluid and may be homogeneous or heterogeneous (for example, containing some colloidal liquid droplets or solid particulates)) flows past and/or through a catalyst material. Preferably the mixture is entirely gaseous. The mixture comprises a source of oxygen and at least one hydrocarbon; in preferred embodiments, the oxygen source is introduced immediately before the catalyst zone or within the reactor catalyst zone or in a staged fashion. A portion of the at least one hydrocarbon reacts to form at least one alkene and/or aralkene and a portion of the source of oxygen reacts to form water. Optionally, the product stream can be rapidly quenched to preserve products and stop further reaction to undesirable products. Quenching can be achieved using integral microchannel quench/heat exchanger to remove heat in adjacent channels to the channels through which the product is flowing. Heat exchange can be between the product stream and the feed stream. In another embodiment, the quench can be achieved by mixing the hot product stream with a cold fluid to rapidly reduce temperature. The quench fluid can be condensable fluids, for example, excess low temperature steam or a condensable hydrocarbon injected as a liquid that evaporates and cools the product stream by absorbing latent heat of evaporation from the hot product stream. Condensable fluids are attractive for use in commercial applications for gas-phase products, since they are relatively easily separated from the product mixture.

This invention discloses methods for the oxidative dehydrogenation of alkane(s) and/or aralkane(s) to alkene(s), alkadiene(s) and/or aralkene(s). The hydrocarbon may be any alkane or aralkane of $C_2$ up to $C_{20}$. Examples of alkane include ethane, propane, isobutane or butane or higher alkanes including up to $C_{20}$ linear and branched alkanes; examples of aralkane include ethylbenzene; examples of alkene for the purpose of this invention include ethylene, propylene and also alkadienes such as butadiene; examples of aralkene include styrene. Preferred examples of hydrocarbons are $C_2$-$C_{18}$ alkanes, preferably $C_2$-$C_{10}$ alkanes, isobutane, propane, ethane, ethylbenzene, or $C_{10}$-$C_{15}$ alkanes such as could be used for making detergent alcohols. The alkanes can be linear, branched and cyclic. Hydrocarbons can be obtained commercially either in pure form or in mixtures. Hydrocarbons can also be derived from other reactions, and the output of these reactions used with or without an intervening purification step. Systems of the invention can be described as including apparatus and/or catalyst in combination with reactants and/or products. By "including" is meant "comprising", however, it will be understood that any of the terms "consists of" or "consists essentially of" may alternatively be used to describe more limited aspects of the invention. Additionally, any of the individual components (such as ethane, for example) may preferably be present in at least 20% purity (based on carbon atoms), or at least 50%, or at least 90%, or 100% purity.

The source of oxygen is preferably a gas capable of providing molecular oxygen, which may conveniently be molecular oxygen or air. Oxygen ($O_2$) is preferred over air, and in preferred embodiments, the $O_2$:$N_2$ ratio (or the $O_2$:diluent ratio) entering a reaction chamber is one or greater, more preferably at least 3, and still more preferably at least 10. In some embodiments, the hydrocarbon/oxygen ($O_2$) ratio in the feed preferably is 2.0 or more, in some embodiments between 1 and 3, in some embodiments 1.8 or less, in some embodiments 2.5 or more.

For autothermal ODH of ethane to ethylene the ethane:$H_2$ feed ratio is preferably in the range 1:0 to 1:1, preferably 1:0.2 to 1:0.6, most preferably 1:0.25 to 1:0.5, and the ethane:O2 feed ratio should remain in the range 1:0.1 to 1:1, preferably 1:0.2 to 1:0.8 and most preferably 1:0.25 to 1:0.5 depending on the overall reaction selectivities and conversion.

The reactant stream may contain diluents such as nitrogen, methane, water vapor, CO, and $CO_2$. Steam, if present in the reactant feed, is preferably present in a steam:C ratio of 5 or less, more preferably 1 or less, and in some embodiments 2 volume % or less. The total diluents to dehydrogenatable hydrocarbons molar ratio is preferably 5:1 or less, more preferably 2:1 or less, preferably less than 50 volume %, more preferably less than 20 volume % diluents in a microchannel reactor, and in some embodiments, less than 2 vol. % diluents. In some preferred embodiments, the hydrocarbons in the reactant stream are at least 75 mol %, more preferably at least 90 mol % of a single hydrocarbon (propane, for example). In some preferred embodiments, the reaction contains no diluent except $H_2$. In order to enhance selectivity, optional hydrogen may be co-fed with the starting hydrocarbon. The hydrogen may be fed from a separate source or produced in the ODH reaction and recycled. In some embodiments, there is no $H_2$ in the reactant stream, in some embodiments there is a 0 to 5 $H_2$:hydrocarbon ratio on a molar basis.

Microchannel reactors are characterized by the presence of at least one reaction channel having a (wall-to-wall, not counting catalyst) dimension of 2.0 mm (preferably 1.0 mm) or less, and in some embodiments 50 to 500 µm. Both height and width are perpendicular to the direction of flow. The height and/or width of the reaction microchannel is preferably 2 mm or less, and more preferably 1 mm or less (in which case the reaction chamber falls within the classical definition of a microchannel). The length of the reaction channel is typically longer. Preferably, the length of the reaction chamber is greater than 1 cm, more preferably in the range of 1 to 25 cm. Typically, the sides of the reaction channel are defined by reaction channel walls. These walls are preferably made of a hard material such as a ceramic, an iron based alloy such as steel, or monel. More preferably, the reaction chamber walls are comprised of stainless steel or inconel which is durable and has good thermal conductivity. The reactors can be made by known methods, and in some preferred embodiments are made by laminating interleaved shims, where shims designed for reaction channels are interleaved with shims designed for heat exchange. A "shim" is a thin flat sheet that optionally has voids to create flow channels or paths.

The reactors preferably include a plurality of microchannel reaction channels and/or a plurality of adjacent heat exchange microchannels. The plurality of microchannel reaction channels may contain, for example, 2, 10, 100, 1000 or more channels. In preferred embodiments, the microchannels are arranged in parallel arrays of planar microchannels. During operation, the heat exchange microchannels contain flowing heating and/or cooling fluids. Non-limiting examples of this type of known reactor usable in the present invention include those of the microcomponent sheet architecture variety (for example, a laminate with microchannels) exemplified in U.S. Pat. Nos. 6,200,536 and 6,219,973 (both of which are hereby incorporated by reference). Performance advantages in the use of this type of reactor architecture for the purposes of the present invention include their relatively large heat and mass transfer rates, and the ability to safely operate in explosive regimes. Unlike conventional reaction vessels for ODH, which have to take into account the possibility of explosion for mixtures of oxygen and hydrocarbon, this is advantageously less of a possibility in the process of the present invention. Furthermore, use of microchannel reactors can achieve better temperature control, and maintain a relatively more isothermal profile, compared to architectures of the prior art. This, in turn, advantageously leads to lessened peak temperatures and lessened coking of the hydrocarbon starting material and/or desired product. Lower peak temperatures also reduce unselective homogeneous gas phase reactions leading to carbon oxides.

An example of microchannel reactor hardware suitable for ODH is shown in FIG. 1A. Coolant microchannels (typically 2 mm or less) are adjacent to a microchannel reaction chamber (2 mm or less). The wall between the channels is preferably 2 mm or less. The flow of coolant may be oriented in a co-current flow, counter-current flow, or cross-current flow.

The length of the process flow channel may be any length, but a typical range is 1 to about 10 inches (2.5 to 25 cm). The height of the process channel may also be any value, but a typical range is 0.1 inches to about 10 inches (0.25 to 25 cm). Each of the process or coolant channel may be further subdivided with parallel subchannels. The spacing of subchannels is dependent upon maximizing heat transfer and minimizing mechanical stresses.

An alternate microchannel design for ODH reactions is the close coupling of an endothermic reaction in an adjacent microchannel. The placement of an endothermic reaction such as a steam reforming reaction next to the exothermic ODH reaction allows for the highest rate of heat transfer. A typical heat flux for convective cooling in a microchannel reactor is on the order of 1-5 W/cm2. The incorporation of a simultaneous endothermic reaction to provide an improved heat sink will enable a typical heat flux of roughly an order of magnitude above the convective cooling heat flux.

Figure 1B:
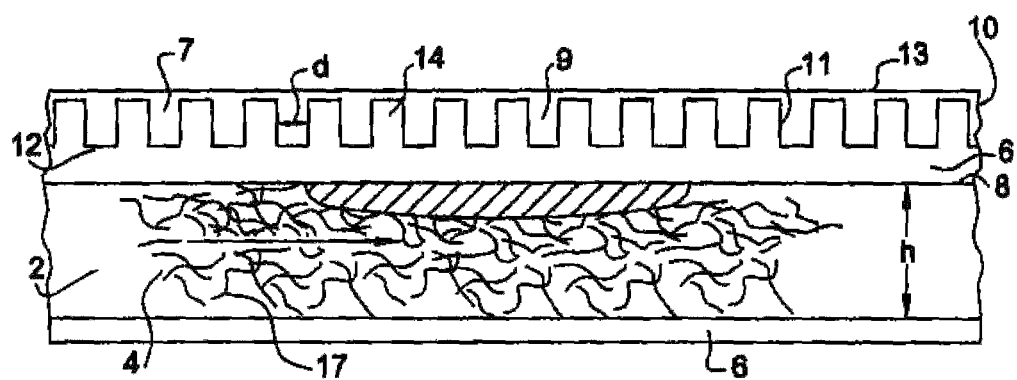
FIG. 1B is a schematic illustration of flow through a reaction chamber.

A simplified representational view of an apparatus of some embodiments of the present invention is illustrated in FIG. 1B. The views shown in the figures are representative examples and should not be understood to limit the invention. A process channel 2 contains a bulk flow path 4. The reaction chamber is defined on two sides by reaction chamber walls 6 and 6'. The internal dimension h (height) is the distance from the surface of the metal wall 8 to the surface of the metal in the opposing wall and does not include the thickness of any oxide layer (not shown). A heating chamber 10 is adjacent to process channel 2. The illustrated heating chamber has fins 11 having a thickness d interleaved with heating channels 14 and a gap 12 between the fins and the channel wall 6. In preferred embodiments, the distance between fins and/or the thickness of the heating chamber is 2 mm, more preferably 1 mm or less. The illustrated embodiment is cross-flow; however, co-flow and counter-flow may also be employed. In some preferred embodiments, an endothermic reaction is occurring in the cooling channel; however, a cool, non-reacting stream could alternatively be used. In some embodiments, the heating chamber 10 is divided into several parts, for example regions 7, 9, 13 into which various fluids could flow to tailor the temperature profile in a process channel. For example, steam or the return portion of a ODH stream could flow through region 7 to provide a preheat zone; an endothermic process stream can flow through region 9 to remove heat from the oxidative dehydrogenation reaction in a reaction chamber (a portion of the process channel in which catalyst 15 is present), and a cold fluid flows through region 13 to quench the reaction.

Figure 2A:
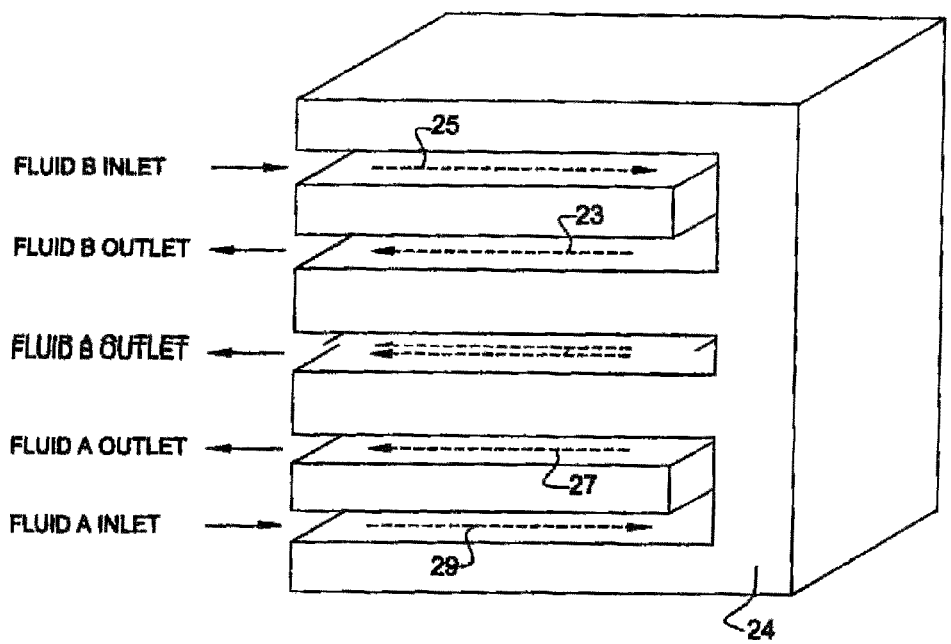
FIGS. 2A and 2B are schematic illustrations of integrated reactor designs showing the process and heat exchange channels and flows.

Another schematic illustration of a cross-section of an integrated reactor design is illustrated in FIG. 2A. A reactant stream (hydrocarbon) and oxygen source flows into the inlet (Fluid B inlet) of a forward process channel, passes through a u-turn, and then flows in the reverse direction in the return process channel. At the same time, a heat transfer fluid flows into the inlet (Fluid A inlet) of a heat transfer channel, passes through a u-turn, and then flows in the reverse direction in the return heat transfer channel. It is desirable to match the coolest portion of the heat transfer channel with the reaction chamber portion of the process channel. In a preferred embodiment, the reaction chamber is located in the return process channel in an area 23 located near the u-turn (closer to the u-turn than the outlet) so that the reactant stream flowing through the forward process channel 25 is warmed by the return process stream (which could be termed the "exhaust" (i.e., the product stream) and the reaction chamber). More preferably, the heat transfer fluid is an endothermic reaction stream that reacts in a catalyst-containing portion located in the return heat transfer channel in an area 27 located near the u-turn opposite the ODH reaction chamber; in which case the endothermic reaction stream in the forward heat transfer channel 29 is preheated by the ODH chamber (the area where there is endothermic reaction catalyst and an endothermic reaction occurs) and exhaust stream. This type of reactor design is especially desirable where the u-turn end 24 (i.e., the hot end) is relatively unconstricted so that it can expand when the device is in operation, manifolds can be connected at the inlet end (i.e., the cold end). As is true of all the reactor designs described herein, the illustrated reactor can be stacked to increase reactor capacity; for example three of the illustrated reactors can be stacked in a single integrated device to have six layers: heat exchange: process: heat exchange: process: heat exchange: process; preferably with all the inlets and outlets located on one side of the device. In some preferred embodiments, the u-turns connect to a single return channel and are not manifolded.

An alternative design, particularly advantageous for operation when the feed gas is adjusted so that the reaction is nearly thermally neutral, excludes the heat exchange channels, increasing reactor capacity. In this embodiment the channels are not interlayered with heat exchange channels but are preferably arranged as stacks of hydrocarbon feed, oxygen feed and product channels, repeating this pattern multiple times.

Figure 2B:
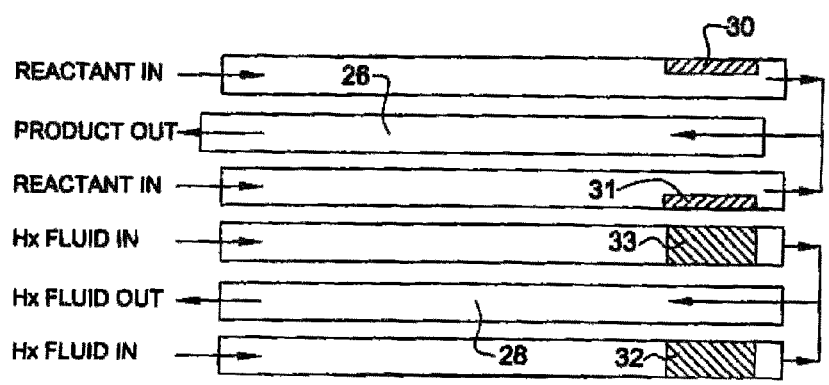

An alternative design is illustrated in FIG. 2B in which return channels 26, 28 are disposed between forward channels. The operation of this device is analogous with the reactor of FIG. 2A, except in preferred embodiments the respective catalysts are located in the forward process 30, 31 and heat exchange channels 32, 33 near the u-turns. Although the catalysts are depicted as partially filling a cross-section of a process channel (such catalysts could be, for example, catalytic inserts), ODH catalysts could fill a cross-section of a process channel (such as, for example, a packed bed). ODH catalysts preferably comprise a wall coating.

Figure 3A:
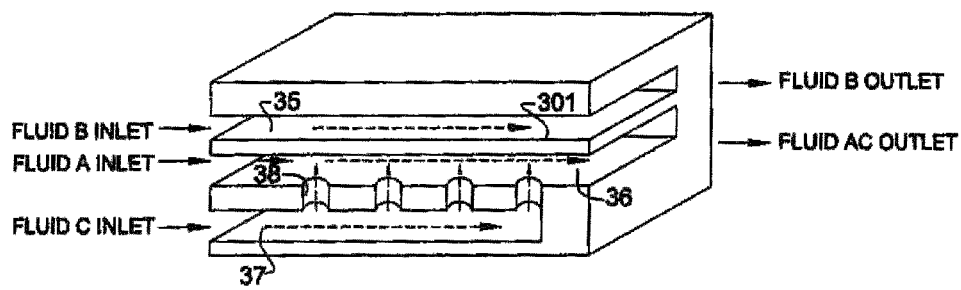
FIGS. 3A-3C are schematic illustrations of integrated reactor designs showing the process and heat exchange channels with distributed flow.
Figure 3B:
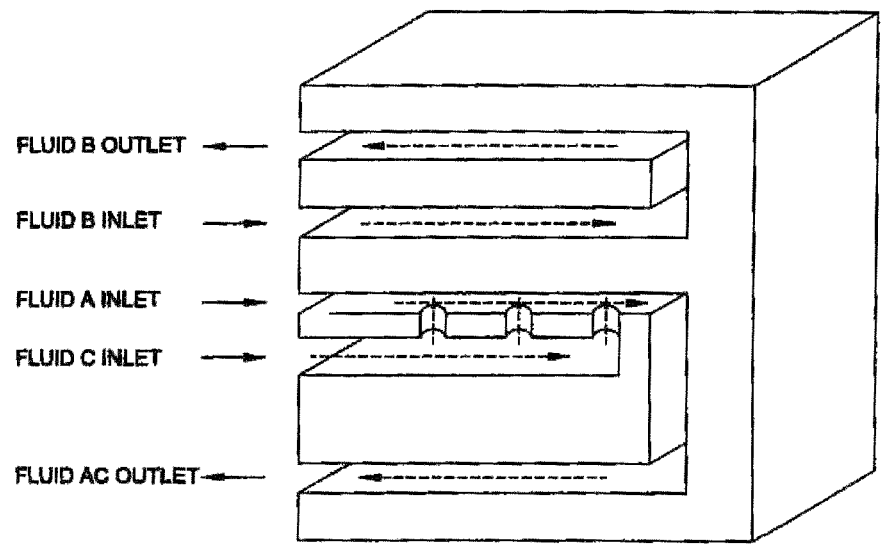
Figure 3C:
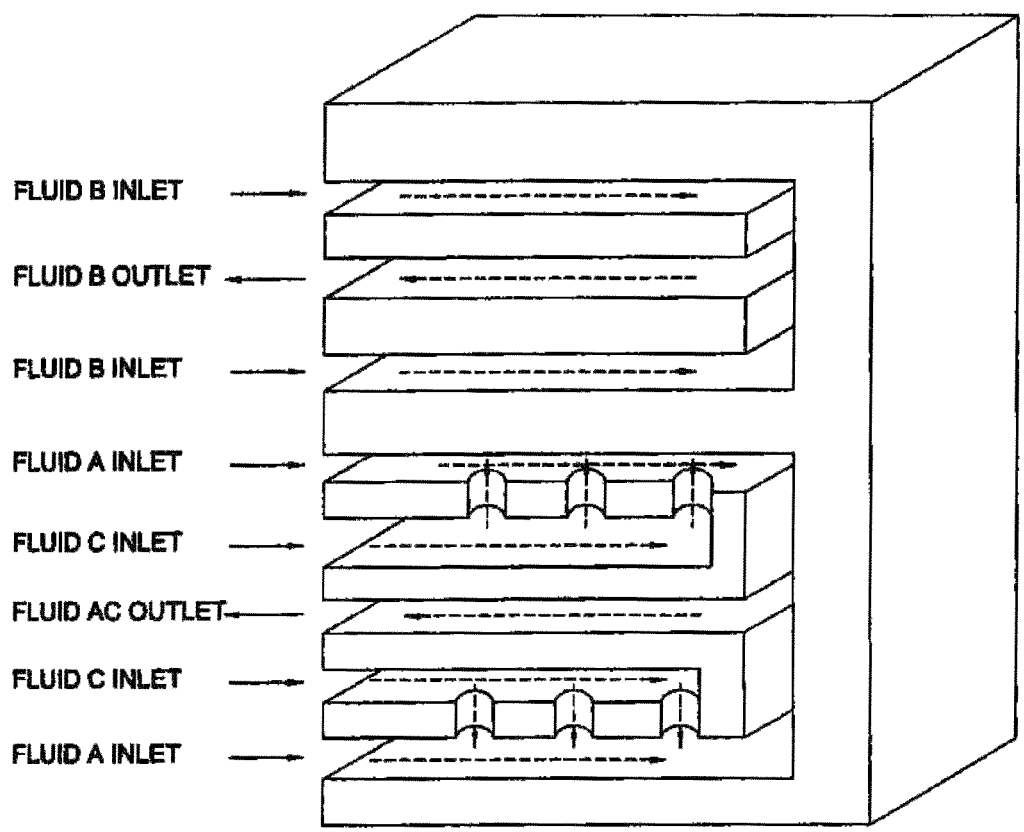

Reactor designs illustrating the distributed flow concept are illustrated in FIGS. 3A-3C. In distributed flow, a secondary fluid enters into a reaction chamber. FIG. 3A illustrates a device in which a first fluid (Fluid B) flows through a first channel 35. Adjacent to this channel is a second channel 36 into which feeds Fluid A. Fluid C enters the reactor in a separate channel 37 and then flows in a distributed fashion through apertures 38 along the length of the second channel. In some embodiments, the first channel contains a oxidative dehydrogenation catalyst (not shown) and a hydrocarbon and oxidant flows into the channel. In some embodiments, the second channel contains an endothermic catalyst (not shown) and either a hydrocarbon or an oxidant flows into the inlet of the second channel (Fluid A Inlet) while, at the same time, another reactant flows into a third channel (Fluid C Inlet) and flows through apertures 38 into the endothermic reaction chamber where an endothermic reaction occurs, in some embodiments there is an endothermic catalyst on wall 301 and the endothermic reaction occurs at or near the wall separating the first and second channels. This controls the rate of endothermic reaction and matches the heat generation rate with the heat required to drive the endothermic reaction. Any thermal profile can be tailored.

Alternatively, a heat transfer fluid (Fluid B) can pass through the first channel. In some preferred embodiments, the first channel 35 contains an endothermic catalyst (not shown) and Fluid B contains an endothermic mixture. A reactant (hydrocarbon) can flow in through either inlet (Fluid A Inlet or Fluid C Inlet) and react over a (oxidative dehydrogenation) catalyst in the second channel 36. When hydrocarbon (optionally containing an oxidant) enters into the third channel 37 (through Fluid C Inlet) it flows in a distributed fashion into the second channel for a controlled reaction over the length of the reaction chamber; in this case, a secondary fluid flows through the second channel. Alternatively, a (hydrocarbon) reactant stream enters through Fluid A Inlet while an oxidant enters Fluid C Inlet and flows into the reaction chamber in a distributed fashion through the apertures. The secondary fluid can be reactive (such as an oxidant) or a nonreactive diluent. A nonreactive diluent can quench the reaction. A cold secondary fluid can be effective in rapidly quenching a reaction.

Alternative designs are illustrated in FIGS. 3B and 3C in which flows can be controlled as have been described in FIG. 2 and FIG. 3A. Channels have been illustrated as open channels but it should be recognized that the channels may contain features such as catalysts, microchannel grooves, and/or support ribs. The illustrated designs assume the typical situation in which the oxidative dehydrogenation reaction is exothermic; however, the invention also includes embodiments in which the reaction is heat-balanced, that is, neither exothermic or endothermic but sufficient oxidation occurs to supply just enough heat to drive the dehydrogenation reactions and make up for heat loss to the environment. In this case the heat exchange channels can optionally be eliminated. In some embodiments, oxidative dehydrogenation occurs to an extent sufficient to have a significant effect on the overall reaction but the oxidation reactions don't generate sufficient heat to make up for the losses to the dehydrogenation reactions and to the environment, in this case, heat needs to be added to the ODH process channel and this heat could be provided, for example, from a hot fluid (or exothermic reaction) in an adjacent heat exchange channel.

Figure 4A:
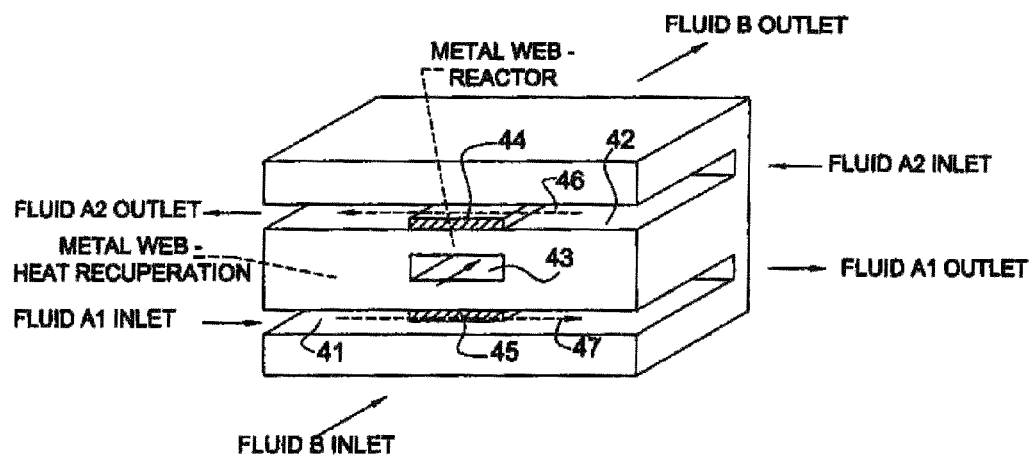
FIGS. 4A and 4B are schematic illustrations of integrated reactor designs with recuperative heat exchange between process streams.
Figure 4B:
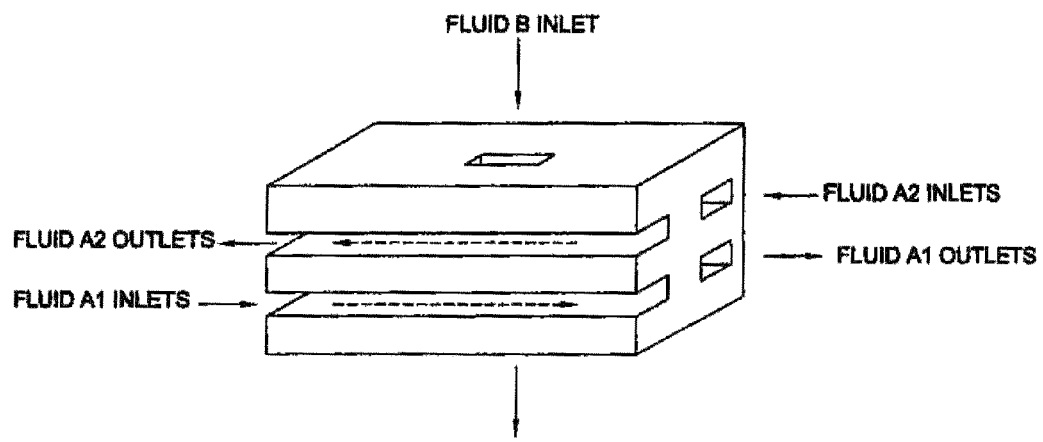

Another way to integrate heat exchange in an integrated reactor is illustrated schematically in FIGS. 4A and 4B. In this embodiment, a first reactant stream (Fluid A1, containing a hydrocarbon and oxidant) flows in a first direction (dashed arrow 47) through a first process channel 41 while a second reactant stream (Fluid A2, containing a hydrocarbon and oxidant) flows in an opposite direction (dashed arrow 46) in a second process channel. Heat exchange is provided to both process channels via an intervening, cross-flow heat exchange channel 43. Preferably, an ODH catalyst 44, 45 is disposed within each process channel 41, 42 on the process channel wall that is adjacent the heat exchange channel to form a reaction chamber within each process channel. Catalyst can optionally be coated on any or all of the walls of the process channel. In cases where a reaction occurs in the heat exchange channels a catalyst may optionally be placed in these channels. The hot product stream exiting the reaction chamber is immediately quenched by thermal transfer with the incoming reactant stream in the adjacent process channel. The illustrated embodiments show the process channels as separated by a constant distance; however, it should be appreciated that the process channels could be positioned closer to each other in the recuperation zones (i.e., the zones where the process channels are adjacent, that is, the zones without an intervening heat exchange channel). Assigning length as the direction parallel to flow within each channel and height as the one direction that is perpendicular to flow in both the process channels and the heat exchange channel, and width being the remaining dimension, it is preferred that the length of each process channel be at least three times, more preferably 10 times longer than the width of the heat exchange channel; and, preferably, the preheat zone of the first process channel is of substantially the same length as the quench or "exhaust" zone of the second process channel, and vice versa. Preferably, the length of the preheat zone of each process chamber is preferably at least as long as the width of the heat exchange channel; similarly, the length of the quench zone of each process chamber is preferably at least as long as the width of the heat exchange channel. It can readily be appreciated that the capacity of this type of device can be increased by stacking up to any desired height with alternating heat exchange and process channels; in some embodiments at least 3 of each.

Figure 5A:
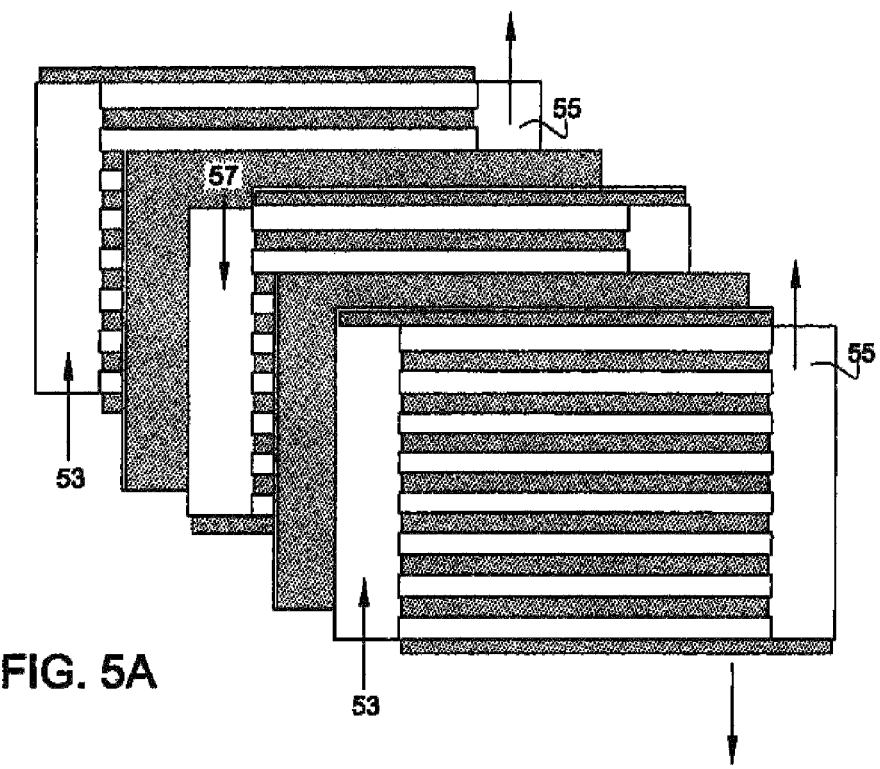
FIGS. 5A and 5B are schematic illustrations of integrated reactor designs that are "numbered up" to achieve greater capacity.
Figure 5B:
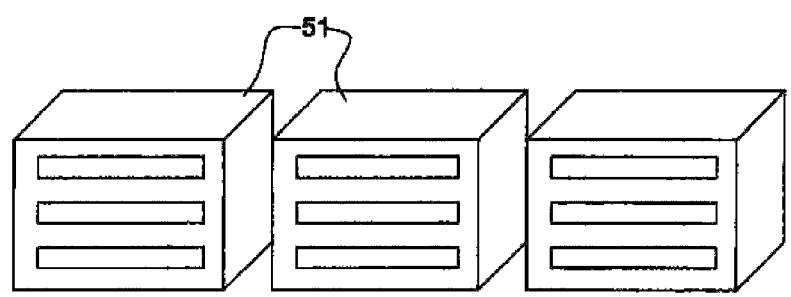

Sheets of channels and/or integrated reactors can be "numbered up" to obtain greater capacity. A schematic illustration of an exploded view of a stack of three identical sheets is shown in FIG. 5A. In a device formed by laminating these three sheets, a first fluid (such as a heated fluid) flows into inlet 53 through the first and third sheets and exits via outlet 55 while a process stream 57 (for example, containing a hydrocarbon) flows through the second sheet. In this figure, the dark regions indicate a solid material, while the white areas indicate areas for fluid flow (such as could be formed by etching). Flow occurs through all the channels. To further increase capacity, blocks 51 of multi-level reactors (see FIG. 5B) can be manifolded and operated together.

It is advantageous to reduce temperature of the product stream as rapidly as possible after leaving the catalyst section of the microchannel reactor to prevent further undesirable reactions of the olefins. This rapid cooling is known as "quenching." An integrated or separate heat exchanger can be used to quench the reaction products, cooling them down rapidly once the reaction has taken place. For example, near the outlet of a reaction channel, cross-flow coolant channels can rapidly cool the product stream. In some preferred embodiments, the heat from the product stream is transferred to a reactant stream in a microchannel heat exchanger, thus preheating a hydrocarbon stream that can be subsequently dehydrogenated. The heat from the product stream could also be used to drive an endothermic reaction. Another form of quench is the rapid addition of a reactive (such as reactant feed) or a non-reactive gas into the hot product stream; this could be accomplished through a gas inlet or inlets located in a reaction chamber, or in or near a reaction chamber outlet, and, optionally with the aid of a static mixer structure within the downstream pipe.

In several of the methods and reaction systems described herein, the reaction products are quickly quenched. Thus, the reaction zone may be closely and integrally linked with a heat exchange zone (either recuperative or other) to quickly cool the reaction mixture after the reactor to below 300° C. or by rapid mixing with secondary, cooler gas stream. Integrated microchannel heat exchanger(s) preferably cool the reaction mixture at a rate greater than 1° C. per millisecond of average heat exchanger residence time; more preferably, at a rate greater than 5° C. per millisecond of average heat exchanger residence time. In some preferred embodiments, the temperature of the process stream decreases by 100, more preferably 200 and still more preferably 300° C. within 50 milliseconds (ms), more preferably 10 ms after reacting (that is, after passing through the hot reaction zone), and in some embodiments 1 ms to 500 ms, preferably 1 ms to 100 ms. Temperatures in reaction microchannels can be measured with thermocouples.

In some embodiments of the inventive reactor or method, the reactor (or method) is configured to send the product stream into a second reactor or recycle the product stream back into the same reactor. There may be intervening separation steps to remove desired products or undesired components or separate hydrogen or a reactant or reactants. In some preferred embodiments, separation is conducted within the same integrated device as the dehydrogenation. Typically, the desired alkene or arylalkene will be separated from the product stream and the unreacted hydrocarbon portion of the product stream recycled.

A product stream containing olefins and unconverted alkanes can be used without further separation as a feedstock for other processes including alkylation. In alkylation, (typically) olefins are reacted with isoalkanes to form higher branched alkanes with high octane numbers suitable for use as components of gasoline. Where the feedstock contains isobutane, the product stream is especially suited as an alkylation feedstock since the products include C3-C5 olefins and unconverted isobutane.

In some preferred embodiments, walls of the reaction channels and/or inner surfaces of conduits and manifolds connected to the reaction channels are coated with a passivation layer. Passivation of surfaces inside the reaction chamber and/or in piping leading to, and/or especially piping leading from the reaction chamber may reduce coking and nonselective oxidation reactions and might enhance time-on-stream performance. Passivation coatings have a different composition than the underlying material. Suitable passivation coatings include a refractory oxide such as silica, alumina, zirconia, titania, chromia, ceria, Group II metals (alkaline earths) and rare earth metals, atomic numbers 57-71. It has been unexpectedly discovered that a silica coating demonstrated superior selectivity compared to an alumina passivation layer. The passivation coating could, optionally, be catalytic supports or could be dense coatings to protect an underlying metal wall. Passivation coatings can be made by applying a sol, or a fine particulate coating onto a metal surface, or applied by chemical or physical vapor deposition or electrochemical deposition, or thermally-grown, or combinations of these techniques. It is believed that surfaces quench undesired gas phase unselective oxidations. Thus, insome embodiments, filler material 17 such as ceramic fibers are placed into the reaction channel in open spaces within the reaction channel that, during operation, would be occupied by hot gas. The filler quenches gas phase reactions and thus improves selectivity.

The reaction channel contains an oxidative dehydrogenation catalyst. Suitable catalyst structures within the reaction channel include porous catalyst materials, monoliths, washcoats, pellets, and powders. The catalyst can comprise a high surface area support and an overlying layer or layers comprising a catalytically active metal or metals. In some preferred embodiments, the reaction is cooled by an adjacent endothermic reaction stream and, in some embodiments, an adjacent heat exchange channel comprises a catalyst that may contain structures such as porous catalyst materials, monoliths, washcoats, pellets, and powders.

The catalytically-active material of the process of the present invention is not particularly limited and may include any effective prior art ODH catalyst. Among the catalytically-active materials of the present invention are the so-called high-temperature catalysts, i.e., those comprising noble metals, preferably catalyst materials comprising at least one metal selected from the group consisting of Pt, Pd, Rh, Ir and Ru. Also among the catalytically-active materials of the present invention are the so-called low-temperature catalysts, which may comprise at least one oxide or phosphate of a metal selected from the group consisting of Li, Mo, V, Nb, Sb, Sn, Zr, Cr, Mg, Mn, Ni, Co, Ce, rare-earth metals (such as Sm), and mixtures thereof. The low or high temperature catalyst may contain additional components such as alkalai or alkaline earth promoters, or metals such as Cu, Ag, or Sn. Preferred support materials include alumina, silica, other metal oxides, mesoporous materials and refractory materials.

Examples of some suitable catalyst compositions are described in U.S. Pat. Nos. 6,130,183 and 5,997,826. Catalysts can be, for example, vanadia dispersed on alumina, or platinum on alumina. Catalysts can also be a noble metal dispersed on a metal oxide layer that is coated over (such as by wash coating or chemical vapor deposition) a metal foam or metal felt (nonwoven metal). In some preferred embodiments, catalyst is disposed (such as by CVD or wash coating) on a wall or walls of a microchannel.

The catalyst can fill up a cross-section of the reaction channel (a flow-through catalyst) or only occupy a portion of the cross-section of a reaction channel (flow-by). In a flow-by catalyst configuration, gas preferably flows in a 0.1-1.0 mm gap adjacent to a porous insert or a thin layer of catalyst that contacts the microchannel wall (in some embodiments, the microchannel wall that contacts the catalyst is in direct thermal contact with a heat exchanger, typically, in these embodiments, a heated fluid or exothermic reaction process stream contacts the opposite side of the wall that contacts the catalyst).

In embodiments, the reaction channel contains a porous catalyst material that defines at least a portion of at least one wall of a bulk flow path. In this preferred embodiment, the surface of the catalyst defines at least one wall of a bulk flow path through which the mixture passes. During operation, the mixture flows through the microchannel, past and in contact with the catalyst. The term "bulk flow path" refers to an open path (contiguous bulk flow region) within the reaction chamber. A contiguous bulk flow region allows rapid gas flow through the reaction chamber without large pressure drops. In preferred embodiments there is laminar flow in the bulk flow region. Bulk flow regions within each reaction channel preferably have a cross-sectional area of $5 \times 10^{-8}$ to $1 \times 10^{-2}$ m$^2$, more preferably $5 \times 10^{-7}$ to $1 \times 10^{-4}$ m$^2$, and the maximum distance from the mid-stream of the bulk flow path is less than 1 mm, preferably less than 0.6 mm. The bulk flow regions preferably comprise at least 5%, more preferably 30-99% of either 1) the internal volume of the reaction chamber, or 2) the cross-section of the reaction channel.

In some preferred embodiments, the catalyst is provided as a porous insert that can be inserted into (or removed from) each channel in a single piece; preferably the porous insert is sized to fit within a microchannel with a width of less than 2 mm. In some embodiments, the porous catalyst occupies at least 60%, in some embodiments at least 90%, of a cross-sectional area of a microchannel. In another embodiment, the catalyst is a coating (such as a washcoat) of material within a microchannel reaction channel or channels.

A "porous catalyst material" (or "porous catalyst") refers to a porous material having a pore volume of 5 to 98%, more preferably 30 to 95% of the total porous material's volume. At least 20% (more preferably at least 50%) of the material's pore volume is composed of pores in the size (diameter) range of 0.1 to 300 microns, more preferably 0.3 to 200 microns, and still more preferably 1 to 100 microns. Pore volume and pore size distribution are measured by Mercury porisimetry (assuming cylindrical geometry of the pores) and nitrogen adsorption. As is known, mercury porisimetry and nitrogen adsorption are complementary techniques with mercury porisimetry being more accurate for measuring large pore sizes (larger than 30 nm) and nitrogen adsorption more accurate for small pores (less than 50 nm). Pore sizes in the range of about 0.1 to 300 microns enable molecules to diffuse molecularly through the materials under most gas phase catalysis conditions. The porous material can itself be a catalyst, but more preferably the porous material comprises a metal, ceramic or composite support having a layer or layers of a catalyst material or materials deposited thereon. The porosity can be geometrically regular as in a honeycomb or parallel pore structure, or porosity may be geometrically tortuous or random. Preferably the support is a foam metal or foam ceramic. The catalyst layers, if present, are preferably also porous. The average pore size (volume average) of the catalyst layer(s) is preferably smaller than the average pore size of the support. The average pore sizes in the catalyst layer(s) disposed upon the support preferably ranges from $10^{-9}$ m to $10^{-7}$ m as measured by $N_2$ adsorption with BET method. More preferably, at least 50 volume % of the total pore volume is composed of pores in the size range of $10^{-9}$ m to $10^{-7}$ m in diameter. Diffusion within these small pores in the catalyst layer(s) is typically Knudsen in nature, whereby the molecules collide with the walls of the pores more frequently than with other gas phase molecules.

At a point where the chamber height or the chamber width is about 2 mm or less, the chamber height and the chamber width define a cross-sectional area. In some preferred embodiments, the cross-sectional area comprises a porous catalyst material and an open area, where the porous catalyst material occupies 5% to 95% of the cross-sectional area and where the open area occupies 5% to 95% of the cross-sectional area. In some preferred embodiments, the open area in the cross-sectional area occupies a contiguous area of $5\times10^{-8}$ to $1\times10^{-2}$ $m^2$. In other preferred embodiments, the catalyst occupies greater than 98% of the cross-sectional area.

If necessary, the catalyst systems can be regenerated by treating the catalyst with an oxidant to oxidize reduced materials formed on or in the catalyst. Typical regeneration oxidants are oxygen or air. Catalysts can be refurbished after irreversible reduction of activity by impregnating or coating the catalyst in situ with additional active materials.

In addition to the reaction microchannel(s), additional features such as microchannel or non-microchannel heat exchangers may be present. Microchannel heat exchangers are preferred. An integrated or separate heat exchanger can be used to quench the reaction products, cooling them down rapidly once the reaction has taken place to prevent further undesirable reactions of the olefins. In some embodiments of the inventive reactor or method, the reactor (or method) is configured to send the product stream into a second reactor or recycle the product stream back into the same reactor. Adjacent heat transfer microchannels enable temperature in the reaction channel to be controlled to promote selective ODH and minimize unselective reactions in the gas phase that increase with temperature. The heat exchange fluids can be gases or liquids and may include steam, liquid metals, or any other known heat exchange fluids—the system can be optimized to have a phase change in the heat exchanger. In some preferred embodiments, multiple heat exchange layers are interleaved with multiple reaction microchannels (for example, at least 10 heat exchanger layers interleaved with at least 10 reaction microchannel layers, where heat exchanger layers are separated by about 2 mm or less.

Many other options exist for the design of a microchannel reactor. For example, a process channel can be in thermal contact with a product channel, an oxygen feed channel, or both. In a simple embodiment, a coolant gas flows in adjacent microchannels to the ODH reaction chamber. The flow of coolant may be cross flow, counter-flow or co-flow. Coflow may be preferred to obtain the greatest heat flux in the beginning of a reaction chamber if the process reaction will be greatest at the front of the reaction chamber where reactants are most concentrated. An improvement to heat transfer would be the use of a higher heat capacity fluid, such as a molten salt or a hot oil. The hot oil coolant is typically limited to systems with reaction temperatures no greater than 400° C. and the molten salts would be used for much higher temperatures.

In an alternate microchannel embodiment, the air or oxygen used for the ODH reaction could be staged or fed sequentially into the reaction mixture. The staging could occur in separate devices, through the use of small orifices or jets within one device, or from a microporous membrane or alternate sparging sheet. The controlled addition of oxygen to partial oxidation reactions, and specifically oxidative dehydrogenation reactions, has been demonstrated in the literature (Tonkovich, Zilka, Jimenz, Roberts, and Cox, 1996, "Experimental Investigations of Inorganic Membrane Reactors: a Distributed Feed Approach for Partial Oxidation Reactions", Chemical Engineering Science, 51(5), 789-806) for distributed feed membrane reactors. Staged oxygen addition (i.e., distributed oxygen feed) lowers the local oxygen partial pressure and thus favors the desired partial oxidation reaction over the competing and undesired combustion reaction. Literature experimental and modeling results demonstrate this effect for series-parallel reactions. The staged addition may also limit peak temperatures by leveling oxygen concentration through the reaction zone.

In some preferred embodiments, an adjacent channel (or channels) carries an oxygen source that is distributed over a length of the reaction microchannel(s). In some preferred embodiments, oxidant enters a reaction chamber at more than 3 points along the chamber length. In some embodiments where a reaction chamber is defined by plural walls (typically four), there are oxidant inlets on one, or more than one, wall of the reaction chamber. The inlets need not be uniformly distributed along the length of the reaction chamber, but positioned for optimal results.

In some preferred embodiments, the hydrocarbon(s) and oxygen-source are mixed such as by a microchannel mixer that is separate or integral with the reaction microchannel. Mixing is preferably conducted before reaction but can be conducted during reaction such as by a mixer disposed within a reaction microchannel.

There is no particular limit on pressure of the reaction. For better economy, pressure should be relatively high. In some preferred embodiments, pressure of the feed is at least 50 kPa, more preferably at least 100 kPa. In some preferred embodiments, pressure of reactants (i.e., excluding partial pressure of diluents) is greater than 1 atm, more preferably greater than 2 atm. Pressure of the feed should be measured prior to contact with the ODH catalyst. In some embodiments, pressure in the reactor is 10 bar or less. In some embodiments, pressure drop through the reactor, or through a reaction channel, is 2 bar or less, an insome embodiments 0.5 bar or less.

Hydrocarbon oxydehydrogenation is conducted at modest pressure, about 1 atm or less, in conventional reactors. Attempts to increase the pressure to higher pressures, greater than 1 atm, 2 atm or more, result in sharp reductions in selectivity to the desired alkene or arylalkene products. As the pressure of the reactant mixture is increased the intensity of heat release, that is the heat release per unit volume, increases proportionally, and the rates of various oxidation reactions increase with the increased partial pressures of the reacting gases. Thus as pressure increases in a conventional reactor the local heat release increases and, due to the limited capability of the conventional reactor to remove heat, the temperature rises. Thus it is not possible to operate conventional reactors at high pressures and high space velocity. With microchannel reactors the high heat removal capacity makes it possible to run reactions at higher pressures and high space velocity and still achieve high selectivity at high conversion. With pressures above 2 atm, preferably above 5 atm, and more preferably above 10 atm and space velocities greater than 10,000 h-1, preferably greater than 100,000 h-1, and more preferably greater than 1,000,000 h-1 it is possible to get good yields of useful products in microchannel reactors.

Hydrocarbon to oxygen ratios in oxidative dehydrogenation reactions are subject to limitations for various reasons. Mixtures containing oxygen and hydrocarbons can be explosive. Indeed, consideration of explosive limits are an important facet of safe plant and process design. Explosive limits become narrower, i.e., more limiting in terms of the acceptable oxygen to hydrocarbon ratio, as pressure increases. The narrower limit of the explosive regime at higher pressure can prevent safe operation of processes at high pressure. Microchannel reactors provide the opportunity to operate in regimes that might otherwise be considered unsafe due to explosive limit considerations. In the microchannel reactor only very small volume mixtures of oxygen and hydrocarbon are available within any one connected region, for example one channel, so that explosions are not expected to propagate among separate channels. Furthermore, the dimensions of the microchannel reactors are similar to the so-called quench diameters of many oxygen/hydrocarbon mixtures. At dimensions below the quench diameter the radical chain reactions that cause explosions are terminated by contact with the device wall, eliminating explosions or flames. Flame arrestors work on this principle. In ODH in microchannels, it is possible to work at pressures above 1 atm, preferably above 2 atm, more preferably above 5 atm, most preferably above 10 atm with high oxygen to hydrocarbon volume ratios, even within the explosive or flammable regimes, oxygen to hydrocarbon ratios greater than 0.2:1, greater than 0.3:1, greater than 0.5:1, even greater than 1:1, without diluents and without explosive reactions.

Preferred temperature ranges of the process of the present invention include: a temperature ranging from 335 to 1000° C., more preferably 500-900 C, and in some embodiments about 500 to about 700. Preferably, during operation, temperature of the catalyst and the adjacent reaction chamber wall differ by less than 10° C.

Gas hourly space velocity (GHSV) of the inventive methods preferably range from 1,000 $h^{-1}$ to 10,000,000 $h^{-1}$ based on reactor volume, or 1,000 ml feed/(g catalyst)(hr) to 10,000,000 ml feed/(g catalyst)(hr). In other preferred embodiments, GHSV is at least 10,000 $h^{-1}$ or at least 10,000 ml feed/(g catalyst)(hr); more preferably at least 100,000 $h^{-1}$ or at least 100,000 ml feed/(g catalyst)(hr); more preferably at least 500,000 $h^{-1}$ or at least 500,000 ml feed/g catalyst; more preferably at least 1,000,000 $h^{-1}$ or at least 1,000,000 ml feed/(g catalyst)(hr).

Liquid hourly space velocity (LHSV) is preferably at least as fast as the examples, e.g., at least 4 $h^{-1}$; more preferably at least 16 $h^{-1}$; more preferably at least 64 $h^{-1}$; more preferably at least 127 $h^{-1}$. Contact times in the reaction chamber (the catalyst zone) preferably are in the range of 0.001 to 5 s, more preferably less than 500 ms, more preferably less than 100 ms, and still more preferably less than about 70 ms. As shown in the following Examples section, we surprisingly found than as contact time decreases, the total olefin yield increases for propane ODH conducted in a microchannel even in the face of stable or decreasing propane selectivity. When the C3:O2 ratio was 2:1 and the process inlet temperature was 540° C. and catalyst bed temperature was 538° C. total olefin yield increased from 21% at 1470 ms contact time to 30.6% at 367 ms contact time. When propane ODH was conducted in a microchannel at a C3:O2 ratio of 2:1 and the process inlet temperature was 597° C. and catalyst bed temperature was approximately 600° C., total olefin yield increases from 29.3% at 250 ms contact time to 33.1% at 82 ms contact time and to 37.8% at 61 ms.

In preferred embodiments employing a quench step, the sum contact times in the precatalyst zone, the catalyst zone and the quench zone is preferably 1 second or less, more preferably 500 ms or less, more preferably 200 ms, and still more preferably 100 ms or less.

The amount of heat that can be transferred through a plane separating the process reaction chamber from a heat exchanger is a function of the method of heat transfer. For convective heat transfer from a hot fluid in a heat exchange channel to a dehydrogenation reaction chamber, the amount of heat (as defined as Watts per square cm of reaction chamber wall area that is adjacent to the heat exchanger) transferred for a gaseous heat transfer fluid is preferably at least 1 $W/cm^2$ and may be up to about 15 $W/cm^2$. For a liquid heat transfer fluid used in convective heat transfer, higher heat transfer fluxes are achievable and may range from at least 1 $W/cm^2$ to about 30 $W/cm^2$. For conductive heat transfer from an exothermic reaction, much higher rates of heat transfer are attainable and heat flux may range from about 10 $W/cm^2$ to about 100 $W/cm^2$. These defined ranges of heat fluxes are for steady-state operation and average over the area of a process reaction chamber wall that is adjacent to a heat exchanger; or, in a reactor with multiple channels (more than two channels), an average over the areas of all dehydrogenation reaction chambers adjacent to heat exchanger(s) in all the channels in operation.

Preferably, selectivity to carbon oxides (on a carbon atom basis) is less than 40%, more preferably less than 20% (in some embodiments, in the range of 20% and 5%), and even more preferably less than 5%. In less preferred embodiments, selectivity to carbon dioxide (on a carbon atom basis) is less than 40%, more preferably less than 20% (in some embodiments, in the range of 20% and 5%), and even more preferably less than 5%.

The $CO/CO_2$ ratio is indicative of the efficiency of the ODH process; low ratios indicate that oxygen was unavailable for ODH and was consumed primarily for combustion. In a microchannel reactor we are capable of obtaining CO to $CO_2$ ratios in excess of those predicted at equilibrium for the particular gas mixture in question when the reactor temperature is below the temperature at which the formation of CO is favoured over the formation of $CO_2$. For example when the ratio of C3 to O2 is 2:1 and the total pressure is 10 psig the temperature at which CO and $CO_2$ are at a 1:1 ratio at equilibrium is approximately 660° C. below this temperature the formation of CO is strongly favored by thermodynamics.

For a given mixture at a given operating pressure the CO:CO2 ratio obtained in a microchannel reactor when the temperature is below that where the formation of CO is thermodynamically favorable and is preferably at least 2.4:1 or more preferably 2.76:1 or more preferably 4.6:1 or even more preferably 10:1.

At equal peak temperatures the volumetric productivity as defined by the grams of target olefin (for example propylene) produced per unit volume of reaction chamber (reaction chamber is that portion of a channel where catalyst is present either as flow-by or flow-through) per hour is greater in a microchannel than in a conventional reactor. As shown in the examples, when the C3 to O2 ratio was 1:1 and the peak temperature was about 625° C. the productivity of the microchannel is greater than that of a quartz tube by a factor of 1.9. Volumetric productivity of a microchannel reactor performing propane ODH could in one instance be 15 g/ml/hr or preferably 30 g/ml/hr or more preferably 60 g/ml/hr or even more preferably 120 g/ml/hr or more, in some embodiments productivity is 15 to about 150 g/ml/hr.

In the case of ethane ODH, at equal average temperatures, the productivity as defined by the grams of target olefin (for example ethylene) produced per unit mass of catalyst of catalyst per hour is greater in the microchannel than in a conventional reactor. When the C2 to O2 ratio was 10:1, the oxidant was air and the average temperature was close to 650° C. the productivity of the microchannel was found to be greater than that of a quartz tube by a factor of 7.4. Productivity of a microchannel reactor performing ethane ODH is preferably at least 270 g/g/hr or more preferably at least 600 g/g/hr or more preferably 1200 g/g/hr or even more preferably at least 2400 g/g/hr.

Once oxidant has been mixed with the hydrocarbon the potential exists for unwanted oxidations to occur (i.e. the production of CO and $CO_2$). The injection of the oxidant into the hydrocarbon stream (or vice versa) just upstream of the catalyst (as was done in the ODH v2 microchannel pellet—see Examples) has the potential to reduce these reactions especially once the gasses are at or near reaction temperature (~400° C.). A pre-catalyst contact time based on the volume between the first point at which the oxidant contacts the hydrocarbon and the point at which the catalyst starts is preferably less than 150 ms or preferably less than 75 ms or more preferably less than 40 ms or even more preferably less than 10 ms.

The rates at which the undesirable combustion reactions proceed are dependent on the total pressure with increased pressure leading to increased rate of reaction in addition they are dependent on the oxidant partial pressure that also increases if the C3:O2 ratio is fixed and the total pressure is increased. These undesirable reactions can be minimized and the selectivities to the desirable olefins maintained if the total inlet pressure is at least 10 atm and the contact time in the pre-catalyst zone is less than 15 ms or preferably less than 7.5 ms or more preferably less than 4.0 ms or even more preferably less than 1 ms. Undesirable reactions can be minimized and the selectivities to the desirable olefins maintained if in a another embodiment the total inlet pressure is at least 20 atm and the contact time in the pre-catalyst zone is less than 7.5 ms or preferably less than 4.0 ms or more preferably less than 2.0 ms or even more preferably less than 0.5 ms. In another embodiment, undesirable reactions can be minimized and the selectivities to the desirable olefins maintained if the total inlet pressure is at least 30 atm and the contact time in the pre-catalyst zone is less than 4.0 ms or preferably less than 2.0 ms or more preferably less than 1.0 ms or even more preferably less than 0.25 ms.

The percent conversion of hydrocarbon (in a single pass) is preferably 10% or higher, more preferably about 20% or higher, more preferably 40% or higher, even more preferably 50% or higher. The level of percent selectivity to desired product or products in the case where more than one valuable alkene can be formed, is preferably at least 10% preferably at least 20%, preferably at least 40%, and in some embodiments 10 to about 60%. The yield of product alkene or alkenes and/or aralkene in mol % per cycle is preferably greater than 10%, and more preferably greater than 20%. The total yield of product alkene or alkenes and/or aralkene(s), in mol %, is preferably greater than 50%, more preferably greater than 75%, and most preferably greater than 85%. The specified levels of conversion, yield and selectivity should be understood as exemplary and include all values such as yield per cycle of at least 15%, at least 25%, etc. as well as ranges such as 10 to 30%. The ranges and conditions can be further understood with reference to the Examples and the invention includes all ranges and minimum levels of conversions, etc. described therein. It is also envisioned that routine testing and experimentation, in view of the teachings provided herein, will reveal superior results and it is therefore intended that this disclosure be broadly interpreted to include descriptions of numerous levels (and ranges) of conditions and results.

Oxygen conversions of greater than 90%, greater than 95%, most preferably greater than 99% can be achieved with gas flow rates of greater than 10,000 h-1, greater than 100,000 h-1 and even greater than 1,000,000 h-1 in an oxidative dehydrogenation process in a microchannel reactor.

While preferred embodiments of the present invention have been described, it will be apparent to those skilled in the art that many changes and modifications may be made without departing from the invention in its broader aspects. The appended claims are therefore intended to cover all such changes and modifications as fall within the true spirit and scope of the invention.

EXAMPLES

Description of Devices

Figure 6:
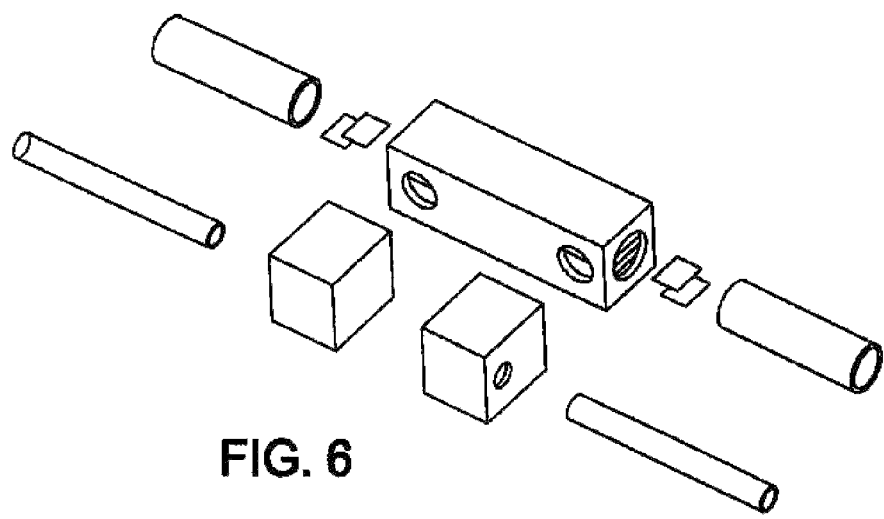
FIGS. 6 and 7 illustrate catalysis testing devices described in the Examples section.

Throughout the Examples section, the term "pellet" does not have its usual meaning, but takes a special meaning of a microchannel testing apparatus as described here. The "ODH v1" microchannel test pellets were designed to provide active cooling on both sides of the process microchannel and use pre-mixed feeds. The ODH v1 pellets were fabricated from 2.8" (7.1 cm) long piece of 0.75" (1.9 cm) Inconel™ 625 bar stock using a combination of wire EDM, plunge EDM, conventional machining and welding. Each device contained 3 microchannels, 1 process microchannel sandwiched between 2 cooling microchannels. Each ran axially and the channels were parallel in alternating planes 0.040" (0.10 mm) apart. The process channel in each device had the dimensions 0.020"×0.300"×2.65" (0.050×0.762×6.73 cm). Each cooling channel had the dimensions 0.020"×0.400"×2.038" (0.050× 1.02×5.17 cm). The cooling microchannels were formed by first opening the channel for the entire length of the device, 2.8" (7.1 cm), and were then isolated from the process channel in the header and footer region by the insertion of 0.395"× 0.306"×0.020" plugs that were subsequently seam welded in place (thus reducing flow length of the channels from 2.65" to 2.038". Access to the cooling channels was obtained at the inlet and outlet ends of the pellet by machining a 0.43" diameter blind hole normal to the major axis of the pellet the depth of which, 0.175", being sufficient to break into the coolant channels but not the reactant. Both header and footer were located on the same face. Washtub type headers were welded in place over the holes at each end. Tubing to allow for the attachment of fittings was welded to the inlet and outlet faces of the tube body and to the coolant headers and footers. An illustration of the device is provided in FIG. 6. Thermowells for 0.020" thermocouples were provided at locations 0.400", 1.067", 1.733" and 2.400" from the inlet face of the process microchannel on the face opposite of the oxidant header and footer. The ODH v.1 pellets were run with heat treatment and passivation layers and without heat treatment or passivation layers.

Figure 7:
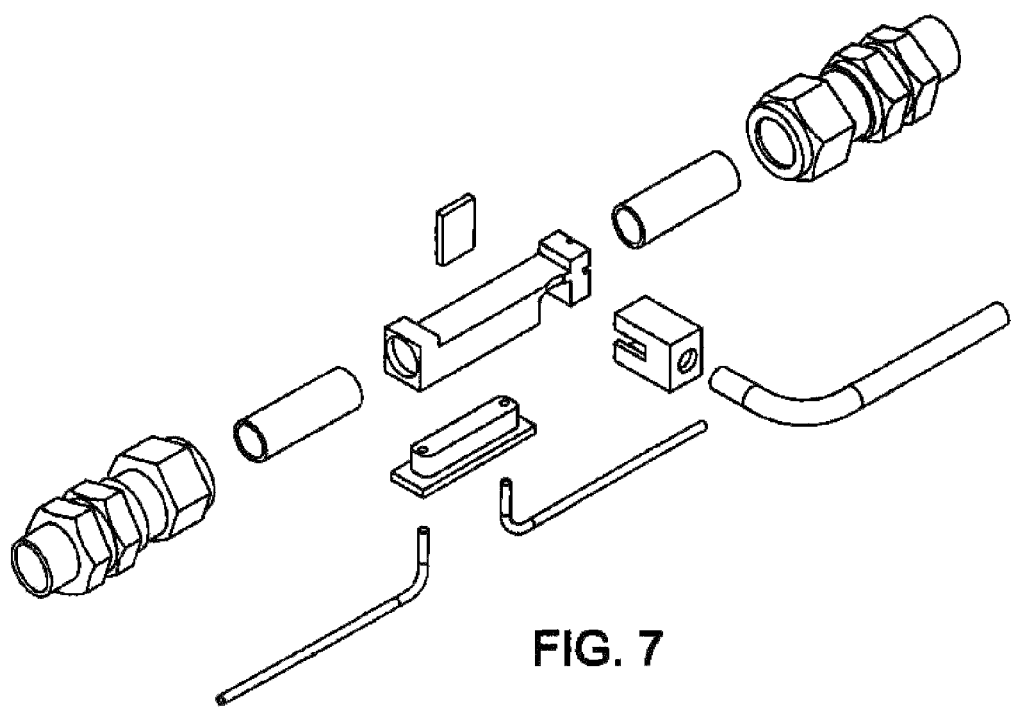

The ODH v.2 pellet was designed to allow active cooling on one face of the microchannel as well as to have the capacity to introduce the oxidant into the reactant in the process microchannel via opposed jets just upstream from the catalyst resulting in a well mixed reactant stream entering the reaction zone. The body of the pellet was fabricated from a 0.625"× 0.500"×2.700" piece of Inconel™ 617 using a combination of wire EDM, plunge EDM, conventional machining and welding (see FIG. 7). A microchannel with an opening of 0.025"×0.300" was then cut into the body. The center line of the channel being 0.250" down the 0.625" side of the 0.500"×0.625" face thus the process microchannel is off-center toward the 'top' of the pellet. The coolant channel is formed by cutting a 0.313" deep by 0.300" wide by 1.500" long pocket in the bottom of the pellet 0.225" from one end of the pellet. The end of the pellet closest to the pocket is then defined as the outlet side of the pellet. The coolant channel was formed when a second piece with a 0.283" tenon is inserted leaving a channel that was 0.030"×0.300" by 1.500". The coolant/process web is 0.0495" thick. Inlet and outlet ports for the coolant are provided at each end of the tenon piece via 0.069" through holes.

Material was removed from the top of the pellet to a depth of 0.187" starting at 0.287" from the inlet face and ending 0.288" from the outlet face. Material was removed from the bottom face to a depth of 0.313" starting at 0.287" from the inlet face and ending 0.787" from the inlet face. The opposing oxygen jets are formed by putting 5 0.020" diameter through holes in the top of the piece. The first two holes have their centres located on a line 0.400" downstream of the inlet face and 0.077" to each side of the device's axial centre line. The center of the third hole is located 0.533" downstream from the inlet face on the axial center line of the device. The final 2 holes have their centres located on a line 0.667" downstream of the inlet face and 0.077" to each side of the device's axial center line. The oxidant header was formed from a washtub type header, 0.490"×0.644"×0.875", with a 0.134"×0.500" slot. This piece was fitted over the area containing the jets and welded in place. Welding on a 0.490"×0.644"×0.063" plate sealed the open face.

Thermowells for 0.020" thermocouples were provided at locations 0.288", 0.725", 1.225" and 1.662" from the outlet face of the process microchannel on the face opposite of the oxidant header and footer.

Prior to use the ODHv.2 devices were cleaned by sonication for 20 min in hexane bath followed by immersion in 20% $HNO_3$ solution for 20 minutes. After the cleaning step the device was subjected to heat treatment protocol (see Table 1).

After heat treatment, the surfaces of the device that come into contact with the reactant hydrocarbons were passivated with an alumina sol-coat (Dispal 14N4-25). This was done by forcing the alumina sol through the reactant inlet tubing, through the reactant microchannel and into the product footer and allowing the sol to remain in contact with the surfaces for 15 min. Excess sol was then removed using nitrogen purge stream flowing through the reactant inlet and, to ensure the jets did not become blocked, simultaneously through the oxidant inlet. After coating the device was calcined by heating to 200° C. at a rate of 1° C./min (to allow it to dry slowly) and then heated to 1000° C. and held there for 1 hour.

TABLE 1

Heat Treatment Protocol employed for ODH v2 pellets

| Step | Temperature | Ramp Rate | Flow/Atmosphere | Total Time | Comments |
| --- | --- | --- | --- | --- | --- |
| 1 | Ambient | 0 | 200 SCCM/$N_2$ | as needed | Vacuum chamber & device 3x and replenish $N_2$ |
| 2 | 900° C. | 3.5° C./min | 84 SCCM/$H_2$ & 200 SCCM/$N_2$ with $H_2O$ vapour | 4 hr 15 min | $N_2$ flows via bubbler with heat tape @ 60° C. |
| 3 | 900° C. | hold | ~1 SLPM/$N_2$ | 30 min | |
| 4 | 1000° C. | 3.5° C./min | 200 SCCM/$N_2$ | 29 min | |
| 5 | 1000° C. | Hold | 200 SCCM/Air | 1 hr | Air @ 1SLPM for first 10 min |
| 6 | 25° C. | 3.5° C./min | 200 SCCM/Air | 4 hr 38 min | |

Two versions of the 'ODH v3' microchannel test pellets were fabricated from 0.5" diameter Inconel 617 rod via a combination plunge and wire EDM and conventional machining. In ODH v3a the process channel was formed by cutting a 0.020"×0.375" axial slot in a 2.003" long piece of the rod material. In ODH v3b the process channel was formed by cutting a 0.035"×0.370" axial slot in a 2.003" long piece of the rod material. In both versions, a 0.73" long by 0.19" deep pocket was then cut on either side of the process channel thus leaving 0.0425" between the inner walls of the process channel and the outside of the pellet.

ODH v3a/b pellets were heat-treated following the protocol in Table 2. After heat-treating a sol-coat of alumina was applied to the surface. This was done by forcing the alumina sol (Dispal 14N4-25) into the process channel and allowing the sol to remain in contact with the surfaces for 15 min. After coating the devices were calcined by heating to 200° C. at a rate of 1° C./min and then heating to 1000° C. with a hold time at the peak temperature of 1 hour. The ODH v3a pellet was tested first with an alumina sol coat and subsequently with a silica sol coat. To form the silica coat, the alumina coat on the ODH v3a pellet was removed by sonication in saturated solution of NaOH for several hours, followed by cleaning the metal surface with acetone. The bare Inconel 617 pellet was then dip-coated with a silica sol (hydrolysed tetraethyl orthosilicate (TEOS) with $HNO_3$) and left to gel for 48 h in air at room temperature. The pellet was then further dried at 80° C. for 1 h followed by calcination (formation of glass) at 1000° C. for 3 h.

TABLE 2

Heat Treatment Protocol employed for ODH v3 Pellets

| Step | Temperature | Ramp Rate | Flow/Atmosphere | Total Time | Comments |
| --- | --- | --- | --- | --- | --- |
| 1 | Ambient | 0 | 200 SCCM/$N_2$ | as needed | Vacuum chamber & device 3x and replenish $N_2$ |

TABLE 2-continued

Heat Treatment Protocol employed for ODH v3 Pellets

| Step | Temperature | Ramp Rate | Flow/Atmosphere | Total Time | Comments |
|---|---|---|---|---|---|
| 2 | 900° C. | 3.5° C./min | 84 SCCM/$H_2$ & 200 SCCM/$N_2$ with $H_2O$ vapor | 4 hr 15 min | $N_2$ flows via bubbler with heat tape @ 60° C. |
| 3 | 900° C. | hold | ~1 SLPM/$N_2$ | 30 min | |
| 4 | 1000° C. | 3.5° C./min | 200 SCCM/$N_2$ | 29 min | |
| 5 | 1000° C. | Hold | 200 SCCM/Air | 10 hr | Air @ 1SLPM for first 10 min |
| 6 | 25° C. | 3.5° C./min | 200 SCCM/Air | 4 hr 38 min | |

Inconel 625 tubes (0.25" nominal O.D., I.D. 0.188") were employed in the ethane ODH testing. Prior to use these tubes were heated to 1000° C. in stagnant air and held at this temperature for 4 hours. Scale was removed via sonication.

Example 1

Propane Oxidative Dehydrogenation in Conventional and Microchannel Reactors

The ODH catalyst used in all the testing of this example was an Mg—V—O catalyst containing 80.9 wt % MgO and 19.1 wt % $V_2O_5$ with surface area of 98 $m^2$/g. Catalyst was pelleted to a size between 250-400 μm (pressed to 5 tons, ground and sieved off the desired fraction) and then pretreated prior to reaction at 500° C. in 40 ml/min $O_2$ for 1 h. In Table 3, "quartz" refers to a 1 cm inner diameter quartz tube containing the packed catalyst.

The exothermicity of the reaction was followed by a thermocouple placed at the bottom of the catalyst bed. For safety reasons, at the beginning of the reaction, nitrogen was introduced into the feed mimicking ODH in air ($O_2$:$N_2$=1:4). Later, in a stepwise way, the diluent was pulled out (ratios of 1:3, 1:2 and 1:1) until it was completely removed. At each step, GC analysis of the reaction effluent was done after 5 min time-on-stream.

higher. At LHSV=157 in the microchannel device there is a slight temperature drop to 512° C., while the conversion and olefin yield increase substantially. Normally at higher throughput (higher LHSV) it would be expected that temperature would increase but in the microchannel the temperature falls slightly. It would also be expected that conversion would fall off at higher LHSVs and not increase as it does here. This surprising result indicates that the microchannel device is operating in a different mode to the conventional fixed bed and producing unexpectedly high yields of useful olefins.

A series of reactions were conducted at ratios of $O_2$:$N_2$ of 4:1, 3:1, 2:1, 1:1, and 1:0 at about 545° C. at varying space velocities in the "blank" quartz tube and the catalyst-containing microchannel reactor. In the blank tube, hydrocarbon conversion remained at less than 10% with propene selectivity of about 60% until diluent was removed ($O_2$:$N_2$=1:0), at which point conversion jumped to 45% while propene selectivity fell to 23% and ethylene selectivity rose from about 7% to about 28%. In the catalyst-containing microchannel reac-

TABLE 3

Effect of LHSV on Conversion and Selectivity in the a Microchannel Pellet
$C_3$:$O_2$ = 1:1, ODH v1

| Device | Quartz Tube | ODH v1* | Quartz Tube | ODH v1* | ODH v1* | ODH v1* | Blank Quartz tube |
|---|---|---|---|---|---|---|---|
| LHSV(v/v//hr) | 4 | 4 | 32 | 32 | 62 | 157 | 62 |
| C3 Conversion (%) | 49.2 | 55.0 | 38.7 | 48.0 | 43.3 | 79.9 | 57.6 |
| Propylene Yield (%) | 21.6 | 16.9 | 15.0 | 11.5 | 9.7 | 13.0 | 13.5 |
| Olefin Yield (%) | 30.9 | 29.0 | 18.6 | 22.1 | 18.5 | 43.6 | 31.0 |
| $CO_x$ Selectivity (%) | 30.0 | 36.8 | 50.7 | 42.7 | 45.3 | 22.1 | 27.6 |
| $CO/CO_2$ Ratio | 1.02 | 1.19 | 1.57 | 1.11 | 1.37 | 4.55 | 6.90 |
| $O_2$ Conversion (%) | 66.8 | 67.3 | 72.3 | 66.4 | 61.2 | 36.9 | 39.9 |
| Selectivity to $CO_2$ (%) | 14.8 | 16.8 | 19.7 | 20.2 | 19.1 | 4.0 | 6.1 |
| Selectivity to CO (%) | 15.1 | 20.0 | 31.0 | 22.5 | 26.2 | 18.2 | 21.4 |
| Selectivity to $CH_4$ (%) | 6.6 | 9.5 | 1.1 | 10.0 | 10.9 | 19.7 | 16.9 |
| Selectivity to $C_2H_6$ (%) | 0.6 | 0.9 | 0.1 | 1.2 | 1.0 | 3.6 | 1.7 |
| Selectivity to Propylene (%) | 43.9 | 30.8 | 38.9 | 23.9 | 22.5 | 16.3 | 23.4 |
| Selectivity to Ethylene (%) | 18.9 | 21.9 | 9.2 | 22.2 | 20.3 | 38.3 | 30.5 |
| Catalyst Bed Temp (° C.) | 540 | 540 | 636 | 540 | 542** | 512 | 538 |

*was not heat treated or given surface coating prior to operation

The results in Table 3 above at a C3:O2 ratio of 1 and an inlet gas temperature of 540° C., show that at the lowest LHSV=4 conversion in the microchannel device is higher than the fixed bed and that overall olefin yield is approximately the same. At LHSV=32, the temperature in the conventional reactor rises to 636° C. while that in the microchannel remains at 540° C. due to the better heat removal properties of the microchannel. Despite the lower temperature in the microchannel, conversion in the microchannel is higher and olefin yield is also tor, at LHSVs of 4, 6 and 32, conversion also rose dramatically to about 50% when diluent was removed and this increase in conversion was accompanied by a substantial increase in ethylene selectivity and in some cases, a modest decrease in propylene selectivity. In each case involving the catalyst-containing microchannel reactor, at LHSVs of 4, 6 and 32, the hydrocarbon conversion and total yield of olefins improved significantly when diluent was removed from the system.

Table 4 below shows the effect of C3:O2 ratio in the microchannel reactor ODH v1

TABLE 4

| LHSV = 32, ODH v1* | | | |
|---|---|---|---|
| C$_3$:O$_2$ | 2 | 1 | 0.5 |
| C3 Conversion (%) | 43.8 | 48.0 | 28.8 |
| Propylene Yield (%) | 19.0 | 11.5 | 9.8 |
| Olefin Yield (%) | 30.6 | 22.1 | 10.9 |
| CO$_x$ Selectivity (%) | 19.2 | 42.7 | 61.5 |

TABLE 4-continued

| LHSV = 32, ODH v1* | | | |
|---|---|---|---|
| C$_3$:O$_2$ | 2 | 1 | 0.5 |
| CO/CO$_2$ Ratio | 2.78 | 1.12 | 0.92 |
| O$_2$ Conversion (%) | 65.3 | 66.4 | 38.5 |
| Selectivity to CO$_2$ (%) | 5.1 | 20.2 | 32.1 |
| Selectivity to CO (%) | 14.1 | 22.5 | 29.4 |
| Selectivity to CH$_4$ (%) | 9.8 | 10.0 | 0.7 |
| Selectivity to C$_2$H$_6$ (%) | 1.2 | 1.2 | 0.1 |
| Selectivity to Propylene (%) | 43.5 | 23.9 | 33.9 |
| Selectivity to Ethylene (%) | 26.4 | 22.2 | 3.9 |
| Catalyst Bed Temp (° C.) | 538 | 540 | 544 |

*was not heat treated or given surface coating prior to operation

At LHSV=32 there is an optimum at C3:O2=2:1 where both propene yield and total olefin yield are maximized and carbon oxides are minimized. As oxygen in the feed increases both propene yield and total olefin yield fall off dramatically. This is surprising since it would be expected that with more O2 in the feed (C3:O2=0.5) there would be more ODH. However, it is believed that with a pre-mixed feed, there will be undesirable gas phase combustion reactions occurring ahead of the catalyst that lead to CO2 formation. This reaction consumes more oxygen than ODH.

$$C3H8+5O2=3CO2+4H2O \quad (1)$$

Versus $$C3H8+0.5O2=C3H6+H2O \quad (2)$$

As the amount of oxygen in the feed decreases, the rate of reaction 1 will also fall and leave more time and oxygen available for ODH resulting in lower carbon oxides and higher yields of desired olefinic products. In view of these unexpected results, with pre-mixed feeds, we would expect that as the C3:O2 ratio falls (more O2 in feed), higher linear velocities (higher LHSVs) would be needed to reduce gas phase reactions occurring before the catalyst bed and optimise conversion to useful products.

Table 5 shows the difference between the quartz reactor and the microchannel reactor ODH v1 at the optimum C3:O2 ratio of 2:1 identified in Table 3 above.

TABLE 5

Comparison of LHSV Effects in a Microchannel Pellet ODH v1 and a Quartz Tube
C$_3$:O$_2$ = 2.:1

| Device | Quartz Tube | ODHv1* | Quartz Tube | ODHv1* | ODHv1* |
|---|---|---|---|---|---|
| LHSV (v/v//hr) | 8 | 8 | 32 | 32 | 157 |
| C3 Conversion (%) | 25.0 | 37.5 | 27.4 | 43.8 | 79.9 |
| Propylene Yield (%) | 12.1 | 13.6 | 12.3 | 19.0 | 13.0 |
| Olefin Yield (%) | 14.0 | 21.0 | 14.2 | 30.6 | 43.6 |
| CO$_x$ Selectivity (%) | 41.6 | 32.8 | 46.6 | 19.2 | 22.1 |
| CO/CO$_2$ Ratio | 1.32 | 1.17 | 1.71 | 2.76 | 4.55 |
| O$_2$ Conversion (%) | 79.5 | 78.9 | 79.4 | 65.3 | 36.9 |
| Selectivity to CO$_2$ (%) | 17.9 | 15.1 | 17.2 | 5.1 | 4.0 |
| Selectivity to CO (%) | 23.7 | 17.7 | 29.4 | 14.1 | 18.2 |
| Selectivity to CH$_4$ (%) | 2.1 | 9.9 | 1.4 | 9.8 | 19.7 |
| Selectivity to C$_2$H$_6$ (%) | 0.2 | 1.3 | 0.1 | 1.2 | 3.6 |
| Selectivity to Propylene (%) | 12.1 | 13.6 | 12.3 | 19.0 | 13.0 |
| Selectivity to Ethylene (%) | 7.7 | 19.7 | 6.9 | 26.4 | 38.3 |
| Catalyst Bed Temp (° C.) | 549 | 538 | 583 | 538 | 512 |

*was not heat treated or given surface coating prior to operation

The table above shows that conversion increases at higher LHSV (shorter contact time). This is again an unexpected result. As stated above normally conversion increases with decreasing LHSV (longer contact time). In the examples in Table 5 we believe that homogeneous gas phase reactions are also occurring ahead of the catalyst zone leading to formation of carbon oxides. These reactions consume more oxygen than ODH.

$$C3H8+5O2=3CO2+4H2O \quad (1)$$

Versus $$C3H8+0.5O2=C3H6+H2O \quad (2)$$

As LHSV increases, linear velocity increases and residence time in the gas phase ahead of the catalyst decreases. This reduces reaction 1 as seen in the examples producing less carbon oxides and leaving more oxygen for the ODH reaction resulting in a higher conversion as shown. Going from LHSV=8 to LHSV=32 in the microchannel reactor ODH v1, the temperature remains constant, selectivity to propylene and ethylene both increase substantially while the selectivity to COx decreases substantially. This contrasts with the quartz fixed bed where the temperature rises, olefin selectivity falls and COx rises.

The overall effect is that at LHSV=32 the olefin yield from the microchannel reactor is more than twice that of the conventional reactor. The data at LHSV 157 at a higher C3:O2 ratio of 1:1, show that the total olefin yield can be increased even higher in the microchannel reactor without having a large increase in temperature which would increase the unselective gas phase reactions and lead to higher yields of carbon oxides in a conventional reactor.

To investigate the effect of surface coatings on the ODH reaction tests were run with alumina and silica coated microchannel reactors ODH v3a at various LHSVs and temperatures. The results are shown in Table 6.

TABLE 6

Effect of Surface Treatment & LHSV on Conversion and Selectivity in a Microchannel Pellet
$C_3:O_2 = 2:1$, ODH v3a

| Surface Treatment | Alumina | Silica | Alumina | Alumina | Silica | Alumina | Silica | Alumina | Silica |
|---|---|---|---|---|---|---|---|---|---|
| LHSV(v/v//hr) | 8 | 8 | 8 | 32 | 32 | 157 | 157 | 157 | 157 |
| C3 Conversion (%) | 19.6 | 24.7 | 14.8 | 17.0 | 24.1 | 16.1 | 21.1 | 40.5 | 32.0 |
| Propylene Yield (%) | 5.9 | 8.2 | 2.4 | 5.2 | 8.5 | 5.5 | 8.5 | 14.3 | 15.2 |
| Olefin Yield (%) | 7.6 | 8.7 | 2.6 | 5.7 | 8.7 | 5.9 | 8.7 | 24.8 | 17.4 |
| $CO_x$ Selectivity (%) | 58.3 | 63.8 | 82.1 | 65.3 | 63.4 | 63.1 | 58.6 | 28.0 | 43.5 |
| $CO/CO_2$ Ratio | 0.71 | 1.21 | 0.66 | 0.75 | 1.18 | 1.37 | 1.55 | 2.11 | 1.59 |
| $O_2$ Conversion (%) | 90.6 | 86.8 | 92.0 | 85.5 | 82.2 | 54.6 | 50.6 | 71.1 | 76.6 |
| Selectivity to $CO_2$ (%) | 33.9 | 28.9 | 49.6 | 37.4 | 29.1 | 26.6 | 23.0 | 9.0 | 16.8 |
| Selectivity to CO (%) | 24.3 | 34.9 | 32.5 | 27.9 | 34.3 | 36.5 | 35.6 | 19.0 | 26.7 |
| Selectivity to $CH_4$ (%) | 2.8 | 0.7 | 0.3 | 0.7 | 0.2 | 0.4 | 0.2 | 9.2 | 2.1 |
| Selectivity to $C_2H_6$ (%) | 0.2 | 0.1 | 0.1 | 0.1 | 0.1 | 0.1 | 0.1 | 1.6 | 0.0 |
| Selectivity to Propylene (%) | 5.9 | 8.2 | 2.4 | 5.2 | 8.5 | 5.5 | 8.5 | 14.3 | 15.2 |
| Selectivity to Ethylene (%) | 8.8 | 2.3 | 1.3 | 3.1 | 1.0 | 1.9 | 1.1 | 26.1 | 7.1 |
| Catalyst Bed Temp (° C.) | 537 | 539 | 499 | 541 | 542 | 552 | 546 | 599 | 631 |

Comparing examples in Table 6 at the same LHSV and temperature it can be seen that the silica coating has a beneficial effect compared to alumina. In these non-optimised experiments, the silica coating gives higher conversions, higher propene selectivity, higher total olefin yields and lower CO2 and methane at all LHSVs.

Example 2

Propane Oxidative Dehydrogenation in Conventional and Microchannel Reactors

The catalyst in this example is the same that was used in Example 1, except that 5 weight % MgO was added as a binder to the powdered catalyst. It was tested in the microchannel device ODH v2 (C in Table 7 below) and in a comparative test in a 4 mm I.D. quartz tube (B in Table 7 below). In the quartz tube, this catalyst demonstrated substantially lower activity compared to the catalyst of Example 1 which was also tested in a larger diameter quartz tube reactor (A in Table 7). The results show that despite the lower performance of this catalyst in a the smaller diameter quartz tube fixed bed reactor, the catalyst out-performs both quartz tube reactors when run in a microchannel reactor ODH v2 at the same temperature as measured in the catalyst bed. Comparing B and C shows that for the same catalyst in the microchannel reactor, conversion is 94% higher, propylene selectivity is approximately the same and propylene yield is 85% higher. Normally in oxidation reactions the selectivity to the desired product falls as conversion increases. Here the results show that despite a very large increase in conversion in the microchannel reactor, selectivity to propene only falls by 1.9%

TABLE 7

Performance of Quartz Tubes vs. the ODH v2 Pellet
LHSV = 32, $C_3:O_2 = 1:1$

| | A. Quartz Tube 10 mm I.D. No binder | B. Quartz Tube 4 mm I.D. +5% MgO binder | C. Microchannel Device ODH v2 |
|---|---|---|---|
| C3 Conversion (%) | 38.7 | 22.7 | 44.0 |
| Propylene Yield (%) | 15.1 | 10.0 | 18.5 |

TABLE 7-continued

Performance of Quartz Tubes vs. the ODH v2 Pellet
LHSV = 32, $C_3:O_2 = 1:1$

| | A. Quartz Tube 10 mm I.D. No binder | B. Quartz Tube 4 mm I.D. +5% MgO binder | C. Microchannel Device ODH v2 |
|---|---|---|---|
| Olefin Yield (%) | 18.6 | 11.9 | 21.9 |
| $O_2$ Conversion (%) | 72.3 | 36.5 | 99.9 |
| Selectivity to $CO_2$ (%) | 19.7 | 23.8 | 25.5 |
| Selectivity to CO (%) | 31.0 | 23.0 | 20.6 |
| Selectivity to $CH_4$ (%) | 1.1 | 3.5 | 3.6 |
| Selectivity to $C_2H_6$ (%) | 0.1 | 0.1 | 0.5 |
| Selectivity to Propylene (%) | 38.9 | 44.0 | 42.1 |
| Selectivity to Ethylene (%) | 9.2 | 8.3 | 7.7 |
| Inlet Gas Temperature | 540° C. | 540° C. | 623° C. |
| Catalyst Bed Temperature* | 636° C. | 627° C. | 628° C. |

*The temperature in the outlet side of the catalyst bed in the tube A, the tube wall temperature at the bottom of the catalyst bed in the tube B or the average web temperature in the ODH v2 pellet Similar tests were conducted for a C3:O2 feed ratio of 2:1 and results are shown in Table 8 below. Test A in Table 8 is for the catalyst from Example 1 (no MgO binder) tested in a 10 mm I.D. quartz tube. Test B is the same catalyst tested in the ODH v1 microchannel reactor. Test C is the catalyst with 5% MgO binder tested in the ODH v2 microreactor. As shown in Table 5 above, comparing A and B shows that the unbound catalyst performs better in a microchannel reactor than a quartz tube fixed bed reactor in terms of conversion and olefins yield. This is even though the temperature rises in the fixed bed (A) by 43° C. and might be expected to increase conversion compared to the microchannel reactors where the temperature is uniform along the channel to within 2 or 3 degrees. Test C shows that the catalyst that is less active in a fixed bed reactor (according to tests A and B in Table 7 above) achieves a superior performance in a microchannel reactor ODH v2 operated at approximately the same catalyst bed temperature as the fixed bed (A). Conversion is increased by 76%, selectivity to carbon oxides is reduced by 33% and olefins yield is increased by 119% over the fixed bed.

TABLE 8

Performance of Quartz Tubes vs. the ODH v2 Pellet
LHSV = 32, $C_3:O_2$ = 2:1

|  | A. Quartz Tube 10 mm I.D No binder | B. Microchannel Device ODH v1 No Binder | C. Microchannel Device ODH v2 +5% MgO |
|---|---|---|---|
| C3 Conversion (%) | 27.4 | 43.8 | 48.4 |
| Propylene Yield (%) | 12.3 | 19.1 | 19.3 |
| Olefin Yield (%) | 14.2 | 30.6 | 31.1 |
| $O_2$ Conversion (%) | 79.4 | 65.3 | 98.7 |
| Selectivity to $CO_2$ (%) | 17.2 | 5.1 | 11.5 |
| Selectivity to CO (%) | 29.4 | 14.1 | 14.7 |
| Selectivity to $CH_4$ (%) | 1.4 | 9.8 | 8.4 |
| Selectivity to $C_2H_6$ (%) | 0.1 | 1.2 | 1.0 |
| Selectivity to Propylene (%) | 44.9 | 43.5 | 40.0 |
| Selectivity to Ethylene (%) | 6.9 | 26.4 | 24.3 |
| Inlet Gas Temperature | 540° C. | 540° C. | 580° C. |
| Catalyst Bed Temperature* | 583° C. | 538° C. | 577° C. |

*The temperature in the outlet side of the catalyst bed in the tube A, the tube wall temperature at the bottom of the catalyst bed in the ODH v1 or the average web temperature in the ODH v2 pellet In Table 9 a comparison is made between the performance of the quartz tube (unbound catalyst) and the microchannel pellet ODH v2 (+5% MgO binder). In this case two differences can be seen between the performance of the quartz tube and the microchannel device. Comparison runs were selected such that the average bed temperatures in the microchannel device were as close as possible to the bed temperature in the quartz tube. The first difference to note is that the microchannel device has its optimal yield of olefins at a C3:O2 ratio of 2:1 while the optimal yield for the quartz tube is at a C3:O2 ratio of 1:1. The location of the optimal yield in the microchannel device is also supported by data reported in Table 4 above. The second difference is that the microchannel device is able to produce a higher yields of both propylene and total olefins at both C3:O2 of 1:1 and 2:1 by operating close to isothermally near the quartz tube catalyst bed temperature.

TABLE 9a

|  | $C_3:O_2$ = 1:1 | | $C_3:O_2$ = 2:1 | |
|---|---|---|---|---|
|  | Tube | ODH v2 | Tube | ODH v2 |
| Conversion of Propane (%) | 38.7 | 44.0 | 27.4 | 46.8 |
| Selectivity to Propylene (%) | 38.9 | 42.1 | 44.9 | 39.3 |
| Propylene Yield (%) | 15.1 | 18.5 | 12.3 | 18.4 |
| Total Olefin Selectivity (%) | 48.1 | 49.8 | 51.8 | 62.5 |
| Olefin Yield (%) | 18.6 | 21.9 | 14.2 | 29.3 |
| Inlet Gas Temperature | 540° C. | 623° C. | 540° C. | 560° C. |
| Catalyst Bed Temperature* | 636° C. | 628° C. | 583° C. | 595° C. |

Table 10 shows the influence of temperature on the on the performance of propane ODH conducted in the microchannel reactor ODH v2 using the bound catalyst at a contact time of 250 milliseconds calculated on total gas flow and a C3:O2 feed ratio of 1:1. The results show that for the catalyst tested the temperature of the device needs to be elevated above 540° C. in order to obtain significant conversion and yields of both C3 and C2 olefins. At C3:O2=1:1, the highest yield seen here is at the highest temperature tested, i.e. 650° C.

TABLE 10

Influence of Temperature in the Microchannel Pellet ODH v2
CT = 250 ms, $C_3:O_2$ = 1:1

| Conversion of Propane (%) | 22.8 | 39.2 | 44.0 | 50.0 |
|---|---|---|---|---|
| Selectivity to Propylene (%) | 37.3 | 42.3 | 42.1 | 38.8 |
| Propylene Yield (%) | 8.5 | 16.6 | 18.5 | 19.4 |
| Total Olefin Selectivity (%) | 39.0 | 46.1 | 49.5 | 51.8 |
| Olefin Yield (%) | 8.9 | 18.1 | 21.9 | 25.9 |
| Inlet Gas Temperature | 541° C. | 597° C. | 623° C. | 648° C. |
| Catalyst Bed Temperature* | 540° C. | 602° C. | 628° C. | 654° C. |

*The average web temperature in the ODH v2 pellet

Table 11 shows similar results for a C3:O2 feed ratio of 2:1. The results show that the temperature at which optimal olefins yield is obtained changes with the ratio of C3:O2. Here the highest yield is seen at 600° C.

TABLE 11

Influence of Temperature in the Microchannel Pellet ODH v2
CT = 250 ms, $C_3:O_2$ = 2:1

| C3 Conversion (%) | 46.8 | 42.9 | 40.3 |
|---|---|---|---|
| Propylene Yield (%) | 18.4 | 17.6 | 17.7 |
| Olefin Yield (%) | 29.3 | 25.4 | 23.4 |
| $CO_x$ Yield (%) | 13.0 | 13.7 | 13.8 |
| $O_2$ Conversion (%) | 99.4 | 99.9 | 100.0 |
| Selectivity to $CO_2$ (%) | 13.4 | 16.9 | 18.9 |
| Selectivity to CO (%) | 14.3 | 15.1 | 15.4 |
| Selectivity to $CH_4$ (%) | 8.7 | 7.9 | 6.8 |
| Selectivity to $C_2H_6$ (%) | 1.1 | 0.9 | 0.9 |
| Selectivity to Propylene (%) | 39.3 | 41.1 | 44.0 |
| Selectivity to Ethylene (%) | 23.2 | 18.2 | 14.0 |
| Inlet Gas Temperature | 596° C. | 623° C. | 647° C. |
| Catalyst Bed Temperature* | 595° C. | 624° C. | 650° C. |

*The temperature in the outlet side of the catalyst bed in the LCIC tube, the tube wall temperature at the bottom of the catalyst bed in the Velocys tube or the average web temperature in the ODH v2 pellet Table 12 shows similar results for a C3:O2 feed ratio of 2.6:1. Here again the highest yield of olefins is seen at 575° C., a lower temperature than at the feed ratios reported above. It appears that the temperature at which 'optimal' yields are obtained increases with decreasing C3:O2 ratio.

TABLE 12

Influence of Temperature in the Microchannel Pellet ODH v2
CT = 250 ms, $C_3:O_2$ = 2.6:1

|  | 575 | 625 |
|---|---|---|
| C3 Conversion (%) | 42.2 | 31.9 |
| Propylene Yield (%) | 18.3 | 15.6 |
| Olefin Yield (%) | 28.1 | 19.1 |
| $CO_x$ Yield (%) | 10.2 | 11.0 |
| $O_2$ Conversion (%) | 98.2 | 99.9 |
| Selectivity to $CO_2$ (%) | 13.8 | 19.3 |
| Selectivity to CO (%) | 10.4 | 15.3 |
| Selectivity to $CH_4$ (%) | 8.4 | 5.4 |
| Selectivity to $C_2H_6$ (%) | 0.9 | 0.0 |
| Selectivity to Propylene (%) | 43.4 | 48.9 |
| Selectivity to Ethylene (%) | 23.2 | 11.1 |
| Inlet Gas Temperature | 578° C. | 623° C. |
| Catalyst Bed Temperature* | 575° C. | 625° C. |

*The temperature in the outlet side of the catalyst bed in the LCIC tube, the tube wall temperature at the bottom of the catalyst bed in the Velocys tube or the average web temperature in the ODH v2 pellet Table 13 shows the influence of $C_3:O_2$ feed ratio at constant temperature in the microchannel pellet ODH v2. When the temperature of the microchannel is held constant and the C3:O2 ratio is changed it can be seen that the propylene yield falls with increasing C3:O2 ratio but that the total olefin yield appears to pass through a maximum in the region of 2:1.

TABLE 13

Influence of $C_3:O_2$ Ratio at Constant Temperature in the Microchannel Pellet ODH v2

| | LHSV = 32 | | |
|---|---|---|---|
| | $C_3:O_2$ = 1:1 | $C_3:O_2$ = 2:1 | $C_3:O_2$ = 2.6:1 |
| Conversion of Propane (%) | 44.0 | 42.9 | 31.9 |
| Selectivity to Propylene (%) | 42.1 | 41.1 | 48.9 |
| Propylene Yield (%) | 18.5 | 17.6 | 15.6 |
| Total Olefin Selectivity (%) | 49.8 | 59.3 | 60.0 |
| Olefin Yield (%) | 21.9 | 25.4 | 19.1 |
| Inlet Gas Temperature | 623° C. | 623° C. | 623° C. |
| Catalyst Bed Temperature* | 628° C. | 624° C. | 625° C. |

*The average web temperature in the ODH v2 pellet

Table 14 below, shows the influence of contact time in the microchannel pellet ODH v2 at constant temperature. As in Table 5. above, the results also show a surprising trend in that conversion increases as contact time over the catalyst decreases. This is opposite to what might be expected in conventional systems where increasing contact time usually results in an increased conversion. Here again we believe that homogeneous gas phase reactions are also occurring ahead of the catalyst zone leading to formation of carbon oxides. These reactions consume more oxygen than ODH.

$$C3H8 + 5O2 = 3CO2 + 4H2O \quad (1)$$

Versus $$C3H8 + 0.5O2 = C3H6 + H2O \quad (2)$$

As contact time decreases, linear velocity increases and residence time in the gas phase ahead of the catalyst decreases. This reduces reaction 1 as seen in the examples producing less carbon oxides and leaving more oxygen for the ODH reaction resulting in a higher conversion, lower COx and higher olefin yields as shown.

TABLE 14

Influence of Contact Time in the Microchannel Pellet ODH v2
$C_3:O_2$ = 2.0:1

| Contact Time (ms) | 61 | 82 | 122 | 250 |
|---|---|---|---|---|
| C3 Conversion (%) | 57.3 | 52.7 | 47.8 | 46.8 |
| Precat. Cntct Time (ms) | 26 | 35 | 53 | 105 |
| Propylene Yield (%) | 18.2 | 19.2 | 18.4 | 18.4 |
| Olefin Yield (%) | 37.8 | 33.1 | 32.1 | 29.3 |
| $CO_x$ Yield (%) | 11.0 | 11.5 | 10.1 | 13.0 |
| $O_2$ Conversion (%) | 96.9 | 97.7 | 99.8 | 99.4 |
| Selectivity to $CO_2$ (%) | 5.6 | 7.0 | 8.3 | 13.4 |
| Selectivity to CO (%) | 13.6 | 14.8 | 12.8 | 14.3 |
| Selectivity to $CH_4$ (%) | 12.6 | 13.1 | 10.2 | 8.7 |
| Selectivity to $C_2H_6$ (%) | 2.2 | 2.2 | 1.6 | 1.1 |
| Selectivity to Propylene (%) | 31.7 | 36.4 | 38.6 | 39.3 |
| Selectivity to Ethylene (%) | 34.3 | 26.5 | 28.5 | 23.2 |
| Inlet Gas Temperature | 597° C. | 597° C. | 597° C. | 596° C. |
| Catalyst Bed Temperature* | 603° C. | 602° C. | 599° C. | 595° C. |

*The temperature in the outlet side of the catalyst bed in the LCIC tube, the tube wall temperature at the bottom of the catalyst bed in the Velocys tube or the average web temperature in the ODH v2 pellet

Example 3

Improved Catalyst Composition Containing Mo $Mg_{4.5}Mo_1V_1O_n$ (or 43.8 wt % MgO; 21.7 wt % $V_2O_5$ and 34.4 wt % $MoO_3$; SA 31 m²/g) and $Mg_{7.75}Mo_{0.1}V_1O_n$ (or 74.8 wt % MgO; 21.7 wt % $V_2O_5$ and 3.5 wt % $MoO_3$) were prepared and tested in the quartz reactor (LHSV=32, $C_3:O_2$=1:1). The results for Mo:V=0.1:1 show similar results as the binary oxides with slightly increased selectivity to propene at the expense of CO. Mo:V=1:1 catalyst gives significantly higher propane conversion and comparable propene selectivity, meaning higher overall yield than Mg—V—O. $CO_x$ selectivity is nearly halved, whereas methane and especially ethylene are significantly increased so that the total olefin yield is doubled. This leads to a much lower exotherm than the conventional catalyst.

| | Mg—V—O vs. Mg—Mo—V—O | | | | |
|---|---|---|---|---|---|
| | Device | | | | |
| | Quartz Tube | Quartz Tube | Quartz Tube | ODHv3a Silica Coated | ODHv3a Silica Coated |
| Catalyst | Mg—V—O | Mg—Mo—V—O | Mg—Mo—V—O | Mg—Mo—V—O | Mg—Mo—V—O |
| Mo:V Ratio | N/A | 0.1:1 | 1:1 | 1:1 | 1:1 |
| $C_3:O_2$ | 1 | 1 | 1 | 1 | 2 |
| C3 Conversion (%) | 38.7 | 38.0 | 65.9 | 16.2 | 10.8 |
| Propylene Yield (%) | 15.0 | 16.1 | 23.0 | 2.4 | 3.6 |
| Olefin Yield (%) | 18.6 | 19.9 | 40.9 | 2.8 | 3.9 |
| $CO_x$ Selectivity (%) | 50.7 | 46.4 | 27.1 | 82.3 | 62.6 |
| $CO/CO_2$ Ratio | 1.6 | 1.2 | 2.5 | 2.1 | 1.6 |
| $O_2$ Conversion (%) | 72.3 | 63.1 | 58.7 | 25.2 | 31.2 |
| Selectivity to $CO_2$ (%) | 19.7 | 20.9 | 7.8 | 26.1 | 24.4 |
| Selectivity to CO (%) | 31.0 | 25.5 | 19.3 | 56.2 | 38.2 |
| Selectivity to $CH_4$ (%) | 1.1 | 1.2 | 8.8 | 0.2 | 0.8 |
| Selectivity to $C_2H_6$ (%) | 0.1 | 0.1 | 2.1 | 0.1 | 0.1 |
| Selectivity to Propylene (%) | 38.9 | 42.4 | 34.9 | 16.1 | 32.9 |
| Selectivity to Ethylene (%) | 9.2 | 9.9 | 27.1 | 1.3 | 3.6 |
| Catalyst Bed Temp (° C.) | 636 | 558 | 583 | 537 | 537 |

Example 4

Ethane Oxidative Dehydrogenation in Conventional and Microchannel Reactors

The ODH catalyst used in the testing for this example was a $Sm_2O_3$—Li—Cl/MgO catalyst containing 5.2 wt % $Sm_2O_3$, 3.4 wt % Li, and 12.5 wt % Cl supported on Mgo. The powder catalyst was pelletized, crushed and sieved into the size range 150-210 μm. The powder form was found to have a surface area of 21 $m^2$/g. Felt based catalysts were prepared by ball milling the native mixed oxide the slurry coating on to the FeCrAlY substrate. The surface area of the felt was found to be 81 $m^2$/g. Prior to use the catalyst was heated in are to 200° C. at 1° C./min and then heated under air to the maximum reaction temperature at a rate of 5° C./min. All testing done on ethane ODH was performed using air as the source of oxygen.

Studies of ethane ODH employing the catalysts described above were performed in various devices, quartz tubes (ID 4 mm), Inconel 625 tubes (ID 4.8 mm) and microchannel pellets ODH v1 and ODH v3b under experimental conditions ranging from C2:O2 ratios of 2:1 to 10.1:1, contact times of 1016 ms to 20 ms and temperatures from 500° C. and 800° C. Illustrative comparisons between the various devices are made in Tables 16, 17 and 18.

A comparison between an blank (containing no catalyst) quartz tube, a quartz tube with powdered catalyst, an Inconel 625 tube with powdered catalyst and an ODH v3b microchannel test pellet containing a felt can be found in Table 16. It can be seen that the inclusion of catalyst increase the conversion of ethane and selectivity to ethylene in both quartz tube (17.0% and 13.0% respectively) and the in the microchannel reactor (19.5% and 15.0% respectively) as compared to the blank (12.5% and 10.9% respectively). The importance of surface passivation can be seen when the results of the quartz tube, Inconel 625 tube and the ODH v3b device are compared. The results for the untreated Inconel 625 tube indicate that the surface promotes combustion resulting in a 67.4% selectivity to COx as compared to 15.5% for the quartz blank and 16.0% for the ODH v3b device. In addition the overall combustion is lower in the Inconel 625 tube, 8.3% as compared to 17.0% in the quartz tube and 19.5% in the ODH v3b device. As was noted in example 1 in the case of propane ODH deep combustion competes with the ODH reaction reducing the overall conversion of ethane. This is further supported by the observation that the microchannel has a greater conversion of ethane and yield of ethylene (19.5% and 15.0%) where the $CO/CO_2$ ratio is 1.46 than the quartz tube (17.0% and 13.0%) where the $CO/CO_2$ ratio is 0.42 (indicating that less oxygen was available for ODH).

TABLE 16

Ethane ODH Performance of Quartz Tubes vs. the ODH v3b Pellet CT = 250 ms, $C_2:O_2$ = 10:1, $Sm_2O_3$ Catalyst, Air as Oxidant

|  | Blank Quartz Tube | Quartz Tube 4 mm ID | IN625 Tube 4.8 mm ID | Microchannel Device ODH v3b** |
|---|---|---|---|---|
| Catalyst Type | None | Powder | Powder | Felt |
| C2 Conversion (%) | 12.5 | 17 | 8.3 | 19.5 |
| Ethylene Yield (%) | 10.9 | 13.0 | 2.6 | 15.0 |
| Olefin Yield (%) | 10.9 | 13.2 | 2.6 | 15.0 |
| $O_2$ Conversion (%) | 0.89 | 100.0 | 100.0 | 99.4 |
| Selectivity to $CO_2$ (%) | 2.2 | 10.9 | 31.0 | 6.5 |
| Selectivity to CO (%) | 6.6 | 4.6 | 36.4 | 9.5 |
| Selectivity to $CH_4$ (%) | 4.1 | 5.8 | 1.6 | 7.1 |
| Selectivity to Propane (%) | 0.3 | 1.1 | 0.0 | 0.0 |
| Selectivity to Propylene (%) | 0.0 | 1.1 | 0.0 | 0.0 |
| Selectivity to Ethylene (%) | 86.8 | 76.6 | 31.0 | 76.9 |
| Inlet Gas Temperature | 650° C. | 648° C. | 658° C. | 652° C. |
| Catalyst Bed Temperature* | 650° C. | 645° C. | 650° C. | 647° C. |

*The tube wall temperature at the bottom of the catalyst bed in the tube or the average external temperature over the catalyst bed in the ODH v3b pellet
**pellet was sol coated with alumina The sensitivity of the performance of ethane ODH conducted in Inconel 625 tubes and ODH v3b microchannel test pellets is demonstrated by data presented in Table 17. It can be seen from the data in Table 17 that at approximately 600° C. the Inconel 625 tubes performed better that the ODH v3b microchannel device in terms of conversion of ethane and selectivity to ethylene but at approximately 645° C. the ODH v3b microchannel device performed much better that the Inconel 625 tube.

TABLE 17

Ethane ODH IN625 Tube vs. Sol Coated DH Pellet CT = 250 ms, $C_2:O_2$ = 2.5:1, $Sm_2O_3$ Catalyst on Felt, Air as Oxidant

|  | IN625 Tube | Microchannel Device IN617 DH Pellet** | IN625 Tube | Microchannel Device ODH v3b** |
|---|---|---|---|---|
| Catalyst Type | Powder | Felt | Powder | Felt |
| C2 Conversion (%) | 16.7 | 11.5 | 23.5 | 29.5 |
| Ethylene Yield (%) | 5.1 | 2.0 | 0.4 | 12.0 |
| Olefin Yield (%) | 5.1 | 2.0 | 0.4 | 12 |
| $O_2$ Conversion (%) | 99.9 | 64.6 | 100.0 | 99.0 |
| Selectivity to $CO_2$ (%) | 65.5 | 76.0 | 36.3 | 38.8 |
| Selectivity to CO (%) | 3.7 | 5.7 | 61.6 | 16.2 |
| Selectivity to $CH_4$ (%) | 0.2 | 1.2 | 0.6 | 4.3 |
| Selectivity to Propane (%) | 0.0 | 0.0 | 0.0 | 0.0 |
| Selectivity to Propylene (%) | 0.0 | 0.0 | 0.0 | 0.0 |
| Selectivity to Ethylene (%) | 30.6 | 17.1 | 1.5 | 40.7 |
| Inlet Gas Temperature | 608° C. | 601° C. | 657° C. | 649° C. |
| Catalyst Bed Temperature* | 589° C. | 600° C. | 641° C. | 645° C. |

*The temperature in the outlet side of the catalyst bed in the LCIC tube, the tube wall temperature at the bottom of the catalyst bed in the Velocys tube or the average external temperature over the catalyst bed in the ODHv3bpellet
**pellet was sol coated with alumina It was desired to not only demonstrate the inherent ability of a microchannel to be operated in a close to isothermal manner and thereby improve selectivity in ODH but to demonstrate as well the ability to apply active cooling adjacent to the channel containing the catalyst and thereby maintain more closely control the reaction conditions. This was attempted in a ODH v1 pellet by operating with and without coolant air flowing in the cooling channels, the results can be seen in Table 18.

From the data it appears that when columns 2 and 3 of Table 18 are compared that the application of active cooling did little to influence the outcome of the ODH reaction. In addition to what is reported here data was collected under several conditions with coolant air flowing at 2200 and 5900 sccm and in all cases no significant influence was noted on the selectivities and conversion. The lack of influence of the application of cooling on the reaction was later traced a fabrication error made in this series of test pellets in which the coolant distribution feature was completely blocked when the coolant channels were sealed. The blocking lead to a situation in which the bulk of the coolant would by-pass the portions of the coolant channel adjacent to the catalyst.

What is apparent from Table 18 is that when a microchannel device is operated close to the measured peak temperature of a quartz tube both the conversion of ethane and selectivity to ethylene are increased and this increase is by approximately the same factor, conversion being increased by 1.87 times and selectivity by 1.84 times.

TABLE 18

Ethane ODH Quartz tube vs. ODH v1 (alumina sol coated) with and without Cooling CT = 20 ms, $C_2:O_2$ = 10:1, $Sm_2O_3$ Catalyst, Air as Oxidant

|  | Quartz Tube | ODH v1 1 Felt, No Cooling | ODH v1 1Felt, 2200 SCCM |
|---|---|---|---|
| C2 Conversion (%) | 7.7 | 14.4 | 14.7 |
| Ethylene Yield (%) | 5.9 | 10.9 | 11.2 |
| Olefin Yield (%) | 6.0 | 10.9 | 11.2 |
| $O_2$ Conversion (%) | 75.1 | N/A | N/A |
| Selectivity to $CO_2$ (%) | 16.2 | 6.7 | 6.7 |
| Selectivity to CO (%) | 1.4 | 11.1 | 10.7 |
| Selectivity to $CH_4$ (%) | 3.5 | 5.5 | 5.4 |
| Selectivity to Propane (%) | 1.6 | 1.2 | 1.1 |
| Selectivity to Propylene (%) | 1.3 | 0.0 | 0.0 |
| Selectivity to Ethylene (%) | 76.1 | 75.5 | 76.1 |
| Inlet Gas Temperature | 618° C. | 669° C. | 665° C. |
| Catalyst Bed Temperature* | 678° C. | 671° C. | 668° C. |

*The tube wall temperature at the bottom of the catalyst bed in the tube or the average external temperature over the catalyst bed in the ODH v3b pellet

We claim:

1. A method of oxidatively dehydrogenating a gaseous hydrocarbon with reduced gas phase reactions, comprising:
   flowing a hydrocarbon-containing fluid and a source of oxygen into a microchannel;
   wherein an oxidative dehydrogenation catalyst is present in the microchannel; and
   wherein the hydrocarbon-containing fluid and the source of oxygen are combined immediately before contacting the catalyst such that precatalyst contact time is 150 ms or less.

2. The method of claim 1 wherein the precatalyst contact time is 75 ms or less.

3. The method of claim 2 wherein the precatalyst contact time is 10 ms or less.

4. The method of claim 1 wherein the product of the system absolute pressure and the precatalyst contact time is less than 150 atmospheres milliseconds.

5. The method of claim 1 wherein the precatalyst contact time is 40 ms or less.

6. The method of claim 1 wherein percent conversion of hydrocarbon (in a single pass) is 20% or higher.

7. The method of claim 6 wherein total yield of product alkene or alkenes and/or aralkenes, in mol %, is preferably greater than 50%.

8. The method of claim 7 wherein oxygen conversion is greater than 95%.

9. A method of oxidatively dehydrogenating a gaseous hydrocarbon with reduced gas phase reactions, comprising:
   flowing a hydrocarbon-containing fluid and a source of oxygen into a microchannel;
   wherein an oxidative dehydrogenation catalyst is present in the microchannel; and
   wherein the combined pressure of hydrocarbon-containing fluid and the source of oxygen in a feed stream is at least 10 atmospheres (when measured under standard conditions) and the precatalyst contact time of the hydrocarbon-containing fluid or the source of oxygen at a temperature of 300° C. or more is 15 ms or less.

10. The method of claim 9 wherein the precatalyst contact time is less than 7.5 ms.

11. The method of claim 9 wherein the precatalyst contact time is less than 2.0 ms.

12. The method of claim 9 wherein the combined pressure of hydrocarbon-containing fluid and the source of oxygen in a feed stream is at least 30 atmospheres (when measured under standard conditions) and wherein the precatalyst contact time is less than 1.0 ms.

13. The method of claim 9 wherein the combined pressure of hydrocarbon-containing fluid and the source of oxygen in a feed stream is at least 30 atmospheres (when measured under standard conditions) and wherein the precatalyst contact time is less than 0.25 ms.

14. The method of claim 9 wherein percent conversion of hydrocarbon (in a single pass) is 40% or higher.

15. A method of oxidatively dehydrogenating a gaseous hydrocarbon, comprising:
   flowing a hydrocarbon-containing fluid and a source of oxygen into a reaction chamber;
   wherein an oxidative dehydrogenation catalyst is present in the reaction chamber;
   wherein the oxidative dehydrogenation catalyst comprises an oxide catalyst comprising Mg, V and Mo, wherein the molar ratio of Mo:V is in the range of 0.5 to 2;
   reacting the hydrocarbon-containing fluid and the source of oxygen, in the reaction chamber, to form water and at least one alkene and/or aralkene.

16. The method of claim 15 wherein the yield of olefins is at least 50% greater than the yield when the reaction is conducted under the same conditions except with a catalyst that contains Mo:V a ratio of 0.1.

* * * * *